(12) United States Patent
Oaks et al.

(10) Patent No.: US 6,245,892 B1
(45) Date of Patent: Jun. 12, 2001

(54) INVAPLEX FROM GRAM NEGATIVE BACTERIA, METHOD OF PURIFICATION AND METHODS OF USE

(75) Inventors: Edwin V. Oaks, Gambrills; Kevin Ross Turbyfill, Waldorf, both of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/408,011

(22) Filed: Sep. 29, 1999

Related U.S. Application Data

(60) Provisional application No. 60/102,397, filed on Sep. 30, 1998, provisional application No. 60/102,398, filed on Sep. 30, 1998, and provisional application No. 60/136,190, filed on May 27, 1999.

(51) Int. Cl.[7] .............................. C07K 14/00; C07K 1/00; G01N 33/53; A61K 45/00
(52) U.S. Cl. ........................ 530/350; 530/416; 435/7.2; 424/282.1
(58) Field of Search ...................................... 530/403, 350, 530/387.1, 416; 424/130.1, 184.1; 435/7.2

(56) References Cited

PUBLICATIONS

Oaks et al, Clinical and Diagnostic Laboratory Immunology, 3: 242–245, Antibody response of monkeys to invasion plasmid antigen D after infection with Shigella spp., Mar. 1996.*

Oaks et al, Infection and Immunity, 53: 57–63, Serum immune response to Shigella protein antigens in Rhesus monkeys and humans infected with Shigella spp., Jul. 1996.*

Lehninger et al., (eds), Principles of Biochemistry, 2nd edition, Worth Publishers, New York, NY, pp. 47 and 138, 1996.*

Karnell et al., Vaccine, 13: 88–99, Safety and immunogenicity study of the auxotropic Shigella flexneri 2a vaccine SFL1070 with a deleted aroD gene in adult Swedish volunteers, 1995.*

* cited by examiner

Primary Examiner—Robert A. Schwartzman
Assistant Examiner—Katharine F Davis
(74) Attorney, Agent, or Firm—Elizabeth Arwine; Charles H. Harris

(57) ABSTRACT

Invaplex, a novel composition comprising invasin proteins and LPS from gram-negative bacteria is described as well as methods of using the novel composition as an adjuvant and a diagnostic tool.

21 Claims, 19 Drawing Sheets

```
VIRULENT SHIGELLAE
         │
         ▼
  WATER EXTRACTION
         │
         ├──▶ DETERMINE TOTAL PROTEIN
         │    CONCENTRATION
         │    SPOT-BLOT FOR PRESENCE OF
         │    IpaB AND IpaC
         ▼
   ION - EXCHANGE
   CHROMATOGRAPHY
        ╱ ╲
       ╱   ╲
      ▼     ▼
  24%B PEAK   50%B PEAK
           ANALYSIS
           IpaB AND IpaC +
           LPS + MEASURE
           TOTAL PROTEIN
      │        │
      ▼        ▼
  INVAPLEX 24  INVAPLEX 50
      │        │
      ▼        ▼
  VACCINATE  VACCINATE
```

FIG. 1

INVAPLEX FROM GRAM NEGATIVE BACTERIA, METHOD OF PURIFICATION AND METHODS OF USE

CROSS-REFERENCE TO RELATED APPLICATIONS

This application claims the benefit of Provisional application Ser. No. 60/102,397, filed Sep. 30, 1998, Provisional application Ser. No. 60/102,398, filed Sep. 30, 1998 and Provisional application Ser. No. 60/136,190 filed May 27, 1999.

FIELD OF THE INVENTION

This invention provides a novel method for purifying Invaplex, a novel composition comprising at least one invasin protein i.e. a protein essential for the process by which a bacterium enters a host cell, and lipopolysaccharide from invasive gram negative bacteria. The composition of the present invention can be used as an adjuvant for vaccines, biochemical, or other substances, and as a diagnostic tool.

INTRODUCTION

Bacillary dysentery is caused by members of the genus Shigella and also enteroinvasive *Escherichia coli* (EIEC). Shigellosis is found in all parts of the world with developing countries accounting for the large majority of cases. A recent report in the Bulletin of the World Health Organization estimates that in developing countries, for children 0–4 years old, there were 113 million Shigella episodes per year and an additional 50 million cases per year in all other age groups. In industrialized countries it is estimated that there are approximately 1.5 million cases of shigellosis per year (Kotloff et al. 1999, *WHO* 77, 651–666). The rampant occurance of antibiotic resistance in Shigella spp. and the high incidence of this disease underscores the need for a vaccine against this human pathogen. However at the present time a vaccine is not commercially available for bacillary dysentery.

The pathogenesis of Shigella is attributed to this organism's ability to invade, reside, and replicate intracellularly within the colonic epithelium. The invasion of host cells by Shigella spp. is a complex multifactorial event in which many different bacterial proteins are involved. Many of the genes for key Shigella virulence proteins are encoded on a large 140 Mdal plasmid. Several of the plasmid encoded proteins called the invasion plasmid antigens (IpaA, IpaB, IpaC, and IpaD proteins) (Buysse et al., 1987, J. Bacteriol. 169, 2561–2569) are essential virulence factors. Similar proteins, called Sip proteins, are made by members of the genus Salmonella (Kaniga et al., 1995, *J. Bacteriol.* 95, 3965–3971). Upon contact or attachment to host cells, the Shigella invasins induce a phagocytic event which results in engulfment and internalization of the bacterium by the host cell. Recent reports have identified that IpaB and IpaC form a complex that can be found in the growth medium of Shigella cultures (Menard et al., 1998, *EMBO J* 13, 5293–5302; Watari et al. 1995, *EMBO J* 14, 2461–2470). The components of this complex are involved in the invasion process, but the actual mechanisms have not been defined (Menard et al., 1994, *Cell* 79:515–525). In addition, purified IpaC has been shown to bind to host cells and participate in the uptake of avirulent shigellae by host cells (Marquart et al., *Infect Immun.* 64:4182–4187, 1996). Involvement in the attachment process and a possible role in the induction of phagocytosis suggests that the invasins or the invasin complex (if it can be isolated) would have adjuvant properties similar to cholera toxin, which also exhibits binding and internalization properties. Furthermore, IpaB, IpaC and IpaD, along with LPS are known major antigens that individuals respond to after infection with shigellae (Li et al. 1993, *Scand. J. Infect. Dis.* 25, 569–577; Oaks et al., 1986, *Infect. Immun.* 53, 57–63; van DeVerg et al. 1992, *J. Infect. Dis.* 166, 158–161). Monkeys or humans infected with shigellae produce antibodies predominantly to IpaB and IpaC, and also produce antibodies at high frequencey to IpaA, IpaD and VirG (another plasmid encoded virulence protein involved in intercellular spreading) (Oaks et al., 1986, supra; Lett et al., 1989, *J. Bacteriol.* 171, 353–359). It is not known if the immune response to the Shigella invasins or more specifically to the invasin complex is crucial to protective immunity.

Adjuvanticity Overview

Many proteins, carbohydrates, and even nucleic acids are not able to induce an immune response in animals unless they are coadministered with an adjuvant. An adjuvant, by definition, is an agent that increases specific immune responses to an antigen that would otherwise be incapable of eliciting an immune response. There are many different types of adjuvants, including aluminum salts (alum), cytokines, surface active agents, and various bacterial products such as Fruend's adjuvant or *Vibrio cholerae* and *E. coli* enterotoxins. Effectiveness of an adjuvant is often dependent upon its ability to stabilize epitope conformation, preserve the antigen from rapid clearance and degradation, and to target the antigen to surface receptors on antigen-presenting cells. Of all the established adjuvants only cholera toxin (CT) and the *E. coli* labile toxin (LT) are purified proteins capable of inducing a potent humoral and mucosal immune response, specifically IgA. In the case of CT, a Th2 T cell response occurs which is characterized by increased levels of IL-4 and IL-5. Among other things, these cytokines lead to increased levels of certain classes of immunoglobulins. Th2 responses are often characterized by higher levels of IgA and the IgGI subclass of IgG. The ability to stimulate a mucosal immune response is a highly desirable property, as most adjuvants are used primarily for systemic immunizations and produce little to no secretory immunity. Unfortunately, CT and LT are toxic molecules and have required genetic modifications to render these adjuvants safe and effective.

In contrast to adjuvants, immunological "carriers" are usually proteins that have haptens or weakly immunogenic molecules covalently attached or genetically incorporated. In addition, living organisms are often used to carry or deliver foreign antigens to the host. Carriers provide T cell help to the antigen and thereby promote the immune response to the antigen.

A safe, effective mucosal adjuvant is desperately needed to promote the immune response to a multitude of new antigens becoming available due to recombinant DNA technology. Delivery of these antigens in a manner which promotes a protective immune response to pathogens depends in large parton an effective adjuvant.

One of the most elusive aspects to understanding how an infected host responds to a pathogen is the indentification of a specific immune response which correlates with protection against future disease. The quest for vaccines to a multitude of pathogens often goes astray because this one single, basic understanding of the immune response to a particular pathogen is not known. In the case of most enteric pathogens this is true.

The primary method for identifying correlates of a protective immune response is the development of a laboratory assay to assess the immune response in infected individuals. A multitude of different assay formats can be used but more often than not it is the antigen used in these assays which is critical. Assays for measuring antibodies, circulating antibody-secreting cells, T cells, cytokines, and other immune effectors are possible.

In the case of Shigella an assay which measures an antibody response which correlates with a protective immune response has not been developed. ELISAs are available for LPS and also the virulence proteins (Ipa proteins) of shigella. However, it has not been possible with any of these assays to demonstrate that a positive antibody response correlates with protection from future disease. The development of an assay which measures an antibody response that correlates with protection will expedite the development and testing of Shigella vaccines. It will also aid in the assessment of a person's immune status with respect to Shigella.

Therefore, there is a need for a diagnostic tool which detects different gram negative bacteria and can measure an antibody response which correlates with protection against future disease.

SUMMARY OF THE INVENTION

The present invention fulfills the needs described above. In this application is described a novel composition comprising at least one invasin protein, a protein essential for bacterial invasion of a host cell, such as IpaA, IpaB, IpaC, and IpaD for Shigella. The invasin protein or proteins of the present invention are complexed with lipopolysaccharide (LPS). The complex of invasion protein or proteins and LPS is in a native conformation and has been termed Invaplex. The Invaplex described below is not only effective as a vaccine against gram-negative bacterial infection but it can also serve as a mucosal adjuvant and a diagnostic tool for detecting antibody response which correlates with protection against future infection.

Our initial experiments were aimed at isolating and purifying IpaC from a water extract of Shigella, a gram-negative bacteria. Usually, IpaC is extracted from growth culture medium. We chose to use the water extract, i.e. the solution resulting from incubating the bacteria with shaking in sterile water, because we hypothesized that the quantity of IpaC would be greater in such an extract. To our knowledge, no protein involved in the invasiveness of gram negative bacteria has been previously isolated from a water extract of gram negative bacteria. To our surprise, when water extract was subjected to various separation techniques such as gel filtration and ion-exchange chromatography, we found that whenever we could detect IpaC from the water extract, we also detected IpaB, IpaD and LPS in the same fractions. We proceeded to design a method to isolate this complex and characterize it. We have developed a method for purifying the Invaplex from intact invasive Shigellae or enteroinvasive *E. coli* (see FIG. 1 for general overview). Briefly, the Invaplex preparations are isolated from virulent, invasive shigellae. A crude mixture is extracted from the shigellae with water. The water extract consists of many proteins and lipopolysaccharide (LPS). The water extract material is then applied to a FPLC ion-exchange column which resolves two key protein peaks, called Invaplex (invasin complex) 24 and Invaplex 50. Fractions containing Invaplex 24 and Invaplex 50 are collected. We found that the complex was composed of many proteins, including IpaB, IpaC, IpaD in addition to LPS. The Invaplex 24 and Invaplex 50 preparations containing Ipa proteins and the LPS form a structure in a completely native configuration and environment. If such a structure is used to immunize animals, it will lead to an immune response directed against a native structure presented by gram-negative bacteria during infection. Mice and guinea pigs immunized with the Invaplex preparations showed a marked serum IgA and IgG response to several different antigens (including the water extract antigen, IpaC and LPS) present in the Invaplex 24 and Invaplex 50 preparations. The two Invaplex preparations were similar in that they both primed the mucosal immune system, but differed in the specificity of the immune response generated. The animals were protected from challenge with gram negative bacteria and immunization with either Invaplex caused no visible distress to the animals. In addition, the highly immunogenic Invaplex can also serve as a very effective mucosal adjuvant very likely due to its ability to interact with the surfaces of host cells and present antigen to the immune system.

Our unpublished data where serum antibodies from recent vaccinees were found to be reactive with the Shigella water extract but poorly reactive with purified Ipa proteins indicates that the Invaplex may be recognized differently (conformationally) than the individual proteins. This suggested that a population of antibodies which specifically react with the complex and not the individual components are produced during an infection and may not be measured in an ELISA using individual purified proteins.

The Invaplex diagnostic assay of the present invention will measure a population of antibodies reactive with a virulence structure. Purified components of the invasin complex such as pure Ipa proteins or pure LPS, are unable to detect this population of antibodies.

Therefore, the present invention relates to a purified composition comprising Invaplex of gram-negative bacteria and methods of using the purified Invaplexes as adjuvants or diagnostic tools. The inventors have purified the Invaplex from two genera of gram-negative bacteria and determined that the complex comprises major antigenic proteins, the invasin proteins (e.g. for Shigella, IpaB, IpaC, and IpaD) as well as LPS. A novel method for purifying the Invaplex from intact bacteria is described.

The Invaplex containing invasin proteins and the LPS forms a structure in a completely native configuration and environment. This results in the ability to react with antibodies that are directed primarily toward epitopes involving the intact structure in addition to antibodies reactive with epitopes that are maintained on purified individual invasin proteins.

Experiments have shown that the Invaplex is also an effective adjuvant which results in very little reactogenicity or toxicity in addition to stimulating a potent mucosal and serum immune response when administered along with the desired antigen.

Therefore, it is one object of the present invention to provide a novel method for the isolation and purification of the Invaplex from gram negative bacteria.

It is another object of the present invention to provide a composition comprising isolated purified Invaplex as a diagnostic tool for detecting gram negative bacteria used as the source of the purified Invaplex.

It is yet another object of the present invention to provide a diagnostic assay for detecting gram-negative bacterial infection having the steps of contacting a sample from a subject suspected of having a gram negative bacterial infection with a purified Invaplex and detecting the presence or absence of a complex formed between the Invaplex and antibodies specific therefor, wherein the presence of a complex indicates presence of gram negative bacterial infection.

Further objects and advantages of the present invention will be clear from the description and claims that follow.

BRIEF DESCRIPTION OF THE DRAWINGS

FIG. 1. Preparation of Invaplex 24 and Invaplex 50 from Shigella spp.

DETAILED DESCRIPTION

Figure 2A:
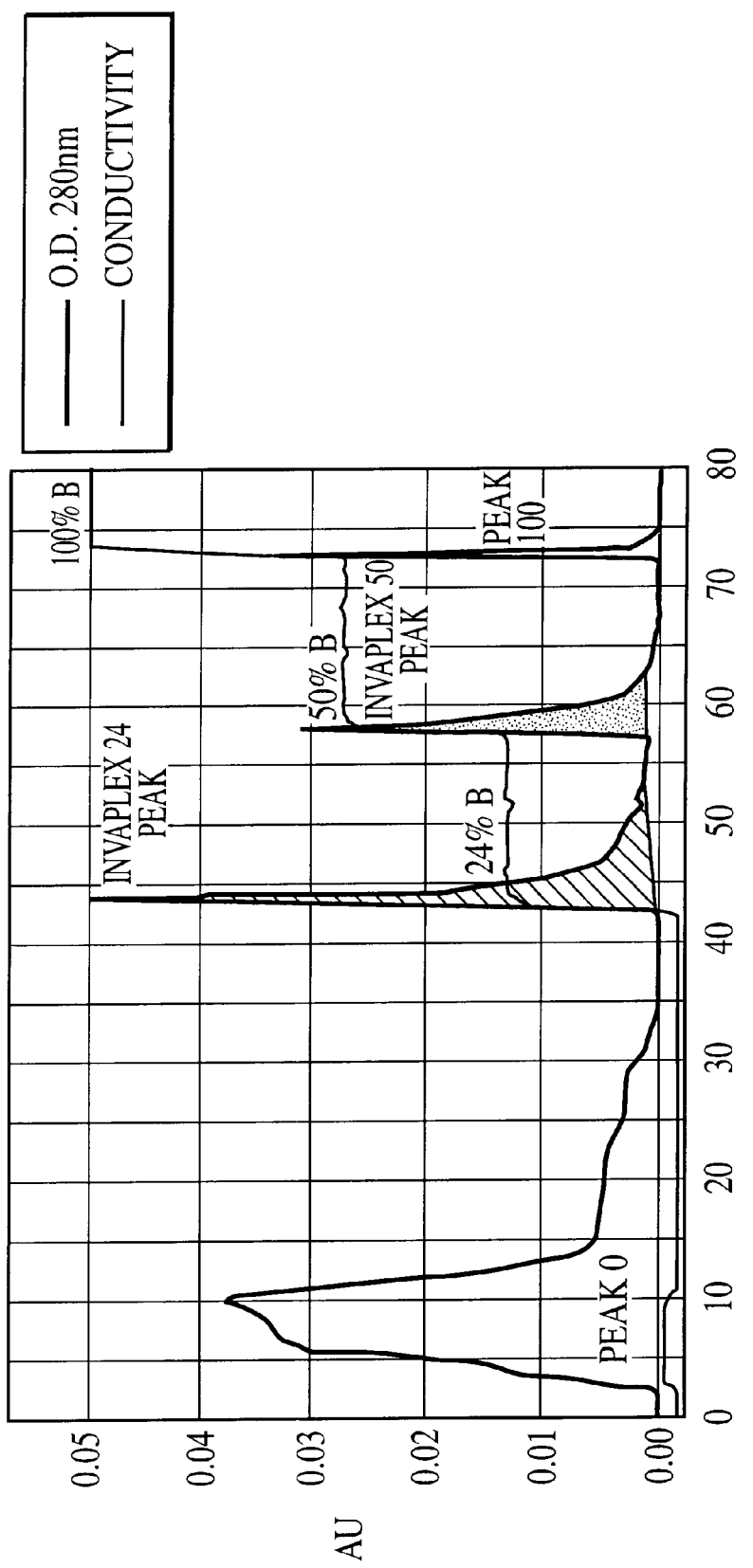
FIGS. 2(A–F). FPLC chromatographs of Invaplex purification by ion-exchange chromatography from *Shigella flexneri* 5, *S. flexneri* 2a, *S. sonnei*, *S. dysenteriae* 1, *S. boydii* 2, and enteroinvasive *Escherichia coli* 0152. FPLC ion-exchange chromatography of water-extracted proteins prepared from *Shigella flexneri* 5 (FIG. 2A), *S. flexneri* 2a (FIG. 2B), *S. sonnei* (FIG. 2C), *S. dysenteriae* 1 (FIG. 2D), *S. boydii* 2 (FIG. 2E), and enteroinvasive *Escherichia coli* 0152 (FIG. 2) were separated on 5 ml columns of anion exchange resin HiTrapQ (Pharmacia). Two tracings are plotted; one is the optical density (O.D.) 280 nm (AU, thick line) which shows the four protein peaks; the other tracing is plotting the conductivity or % buffer B (1M NaCl in 20 mM Tris-HCl, pH 9.0) and clearly shows the 24%, 50%, and 100% buffer B steps. The flow rate was 2.0 ml/min and 2 ml fractions were collected throughout the run. The Invaplex 24 and Invaplex 50 peaks are labeled. These fractions are collected and used in further experiments. All fractions are analyzed for IpaC and IpaB content by spot blot. Peak IpaC and IpaB content is in the Invaplex 24 and Invaplex 50 peak fractions.
Figure 2B:
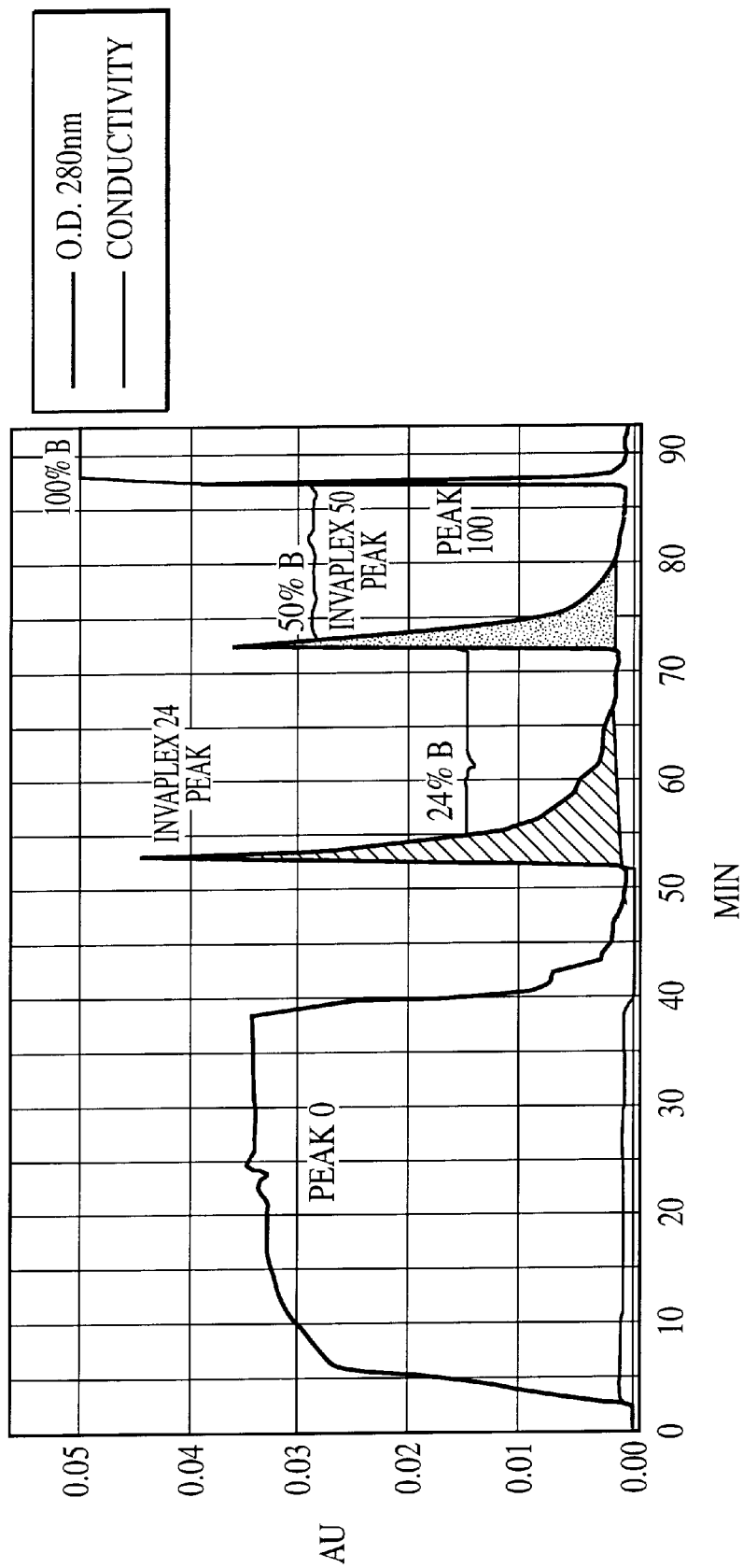
Figure 2C:
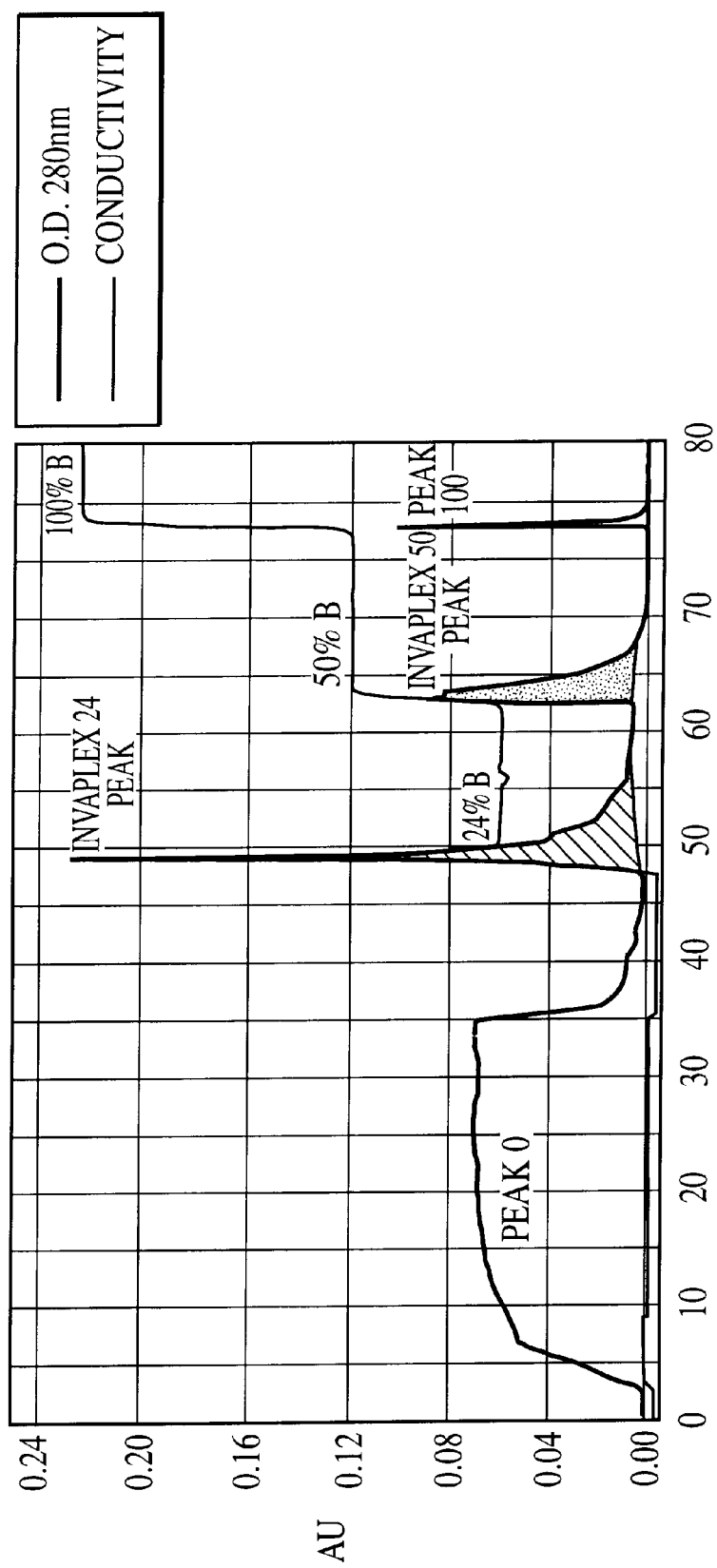
Figure 2D:
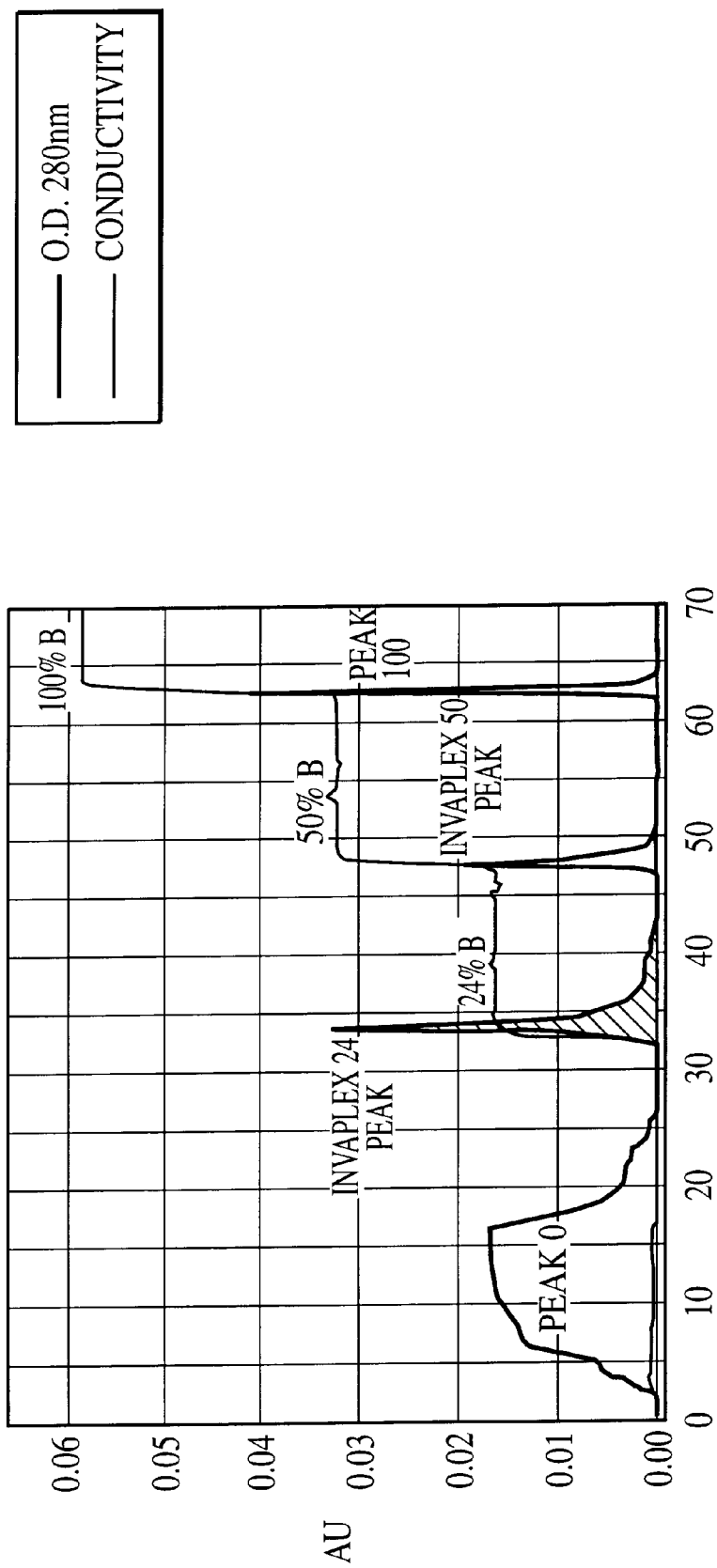
Figure 2E:
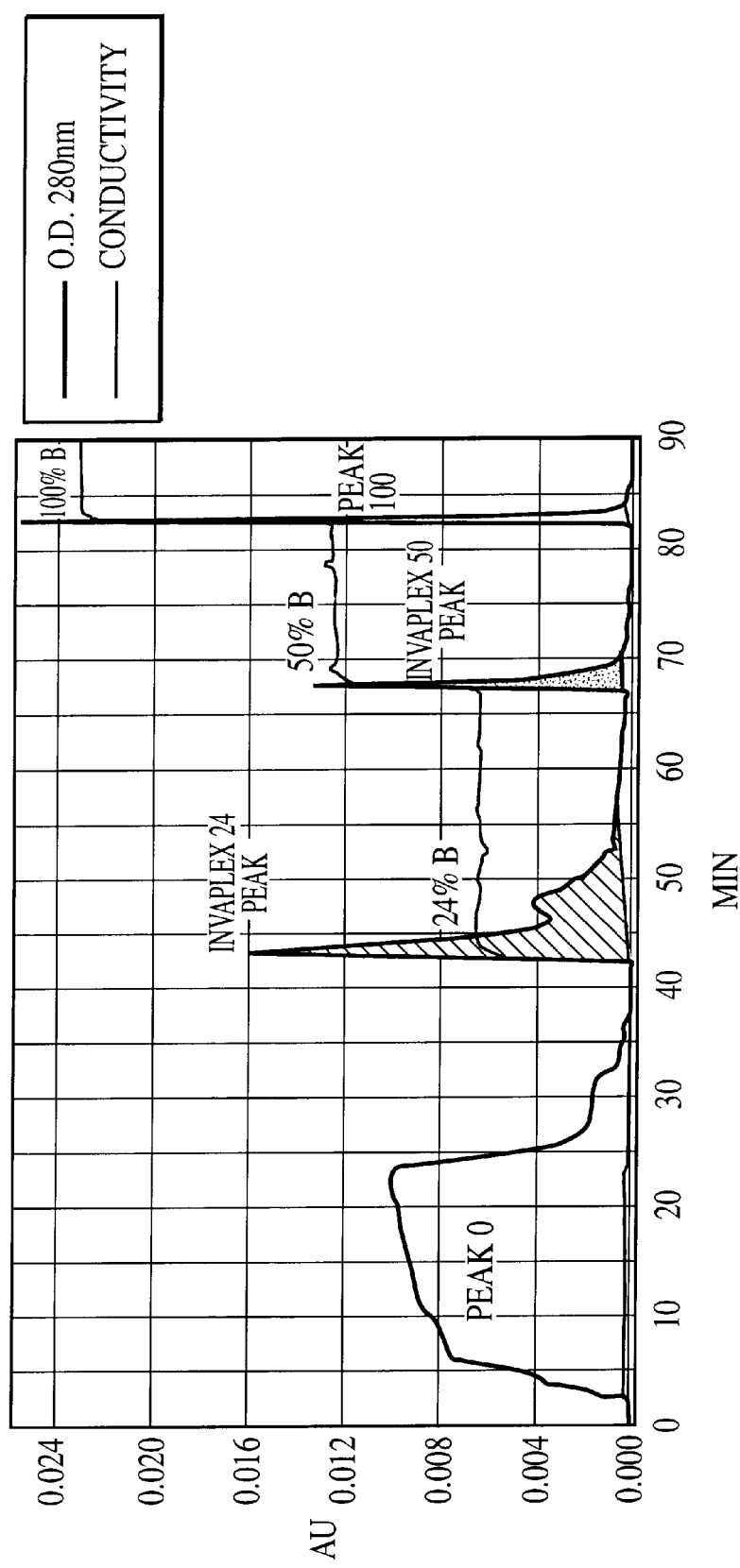
Figure 2F:
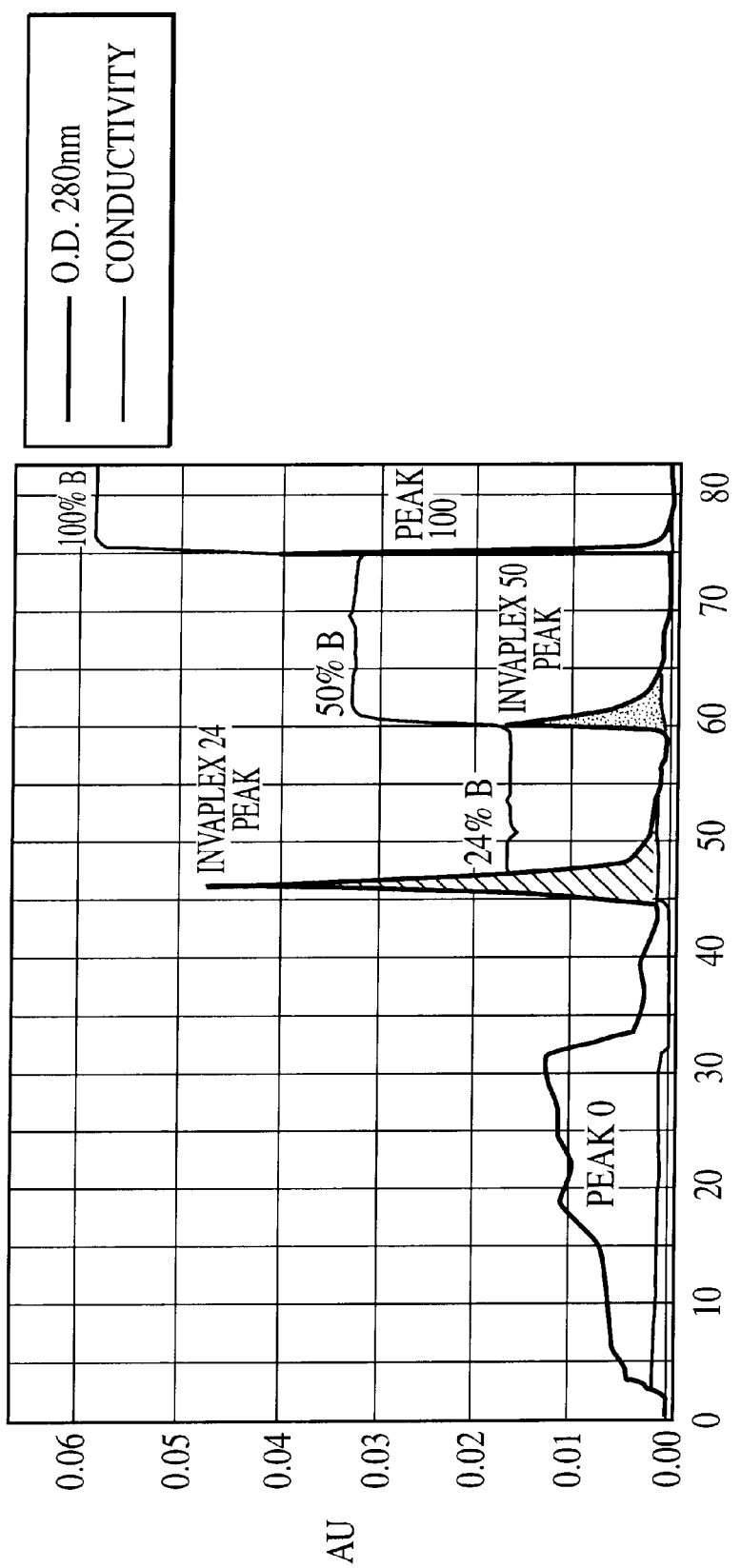

The present invention relates in part to a method for isolating purified Invaplex from gram-negative bacteria.

Invaplex can be prepared from any gram-negative bacteria including but not limited to those classified under the following genera, Shigella, Escherichia, Salmonella, Yersinia, Rickettsia, Brucella, Erhlichiae, Edwardsiella, Campylobacter, Legionella and Neisseria. These are all invasive bacteria that have a gram negative architecture (i.e. they have an inner or cytoplasmic membrane and an outer membrane surrounding the inner membrane).

In addition to wild type virulent gram-negative bacteria, mutants of these organisms may be useful, such as those which hyper-express quantities of invasin proteins and which might lead to the production of more Invaplex. The gene virF, for example is involved in the regulation of Ipa proteins in shigellae (Sakai et al. 1988, Mol. Microbiol. 2, 589–597). All documents cited herein supra and infra are hereby incorporated in their entirety by reference thereto. Furthermore, it may be beneficial to perpare Invaplex from bacteria mutated in toxin genes so that the organism does not produce toxin, for example Shiga toxin. Invaplex prepared from tox-strains would be potentially safer because potential contamination by the toxin would be eliminated.

Increased levels of Invaplex may be achieved by extracting the complex in the presence of chemicals that stimulate secretion of the invasin proteins. Such chemicals include Congo Red, Evans Blue and direct orange (Bahrani, F. K, Infect Immun 65:4005–4010, 1997). These chemicals could be added during the water extraction or during the growth of the bacteria.

In order to isolate the invasin proteins (Ipa proteins or similar proteins in other invasive bacteria), the invasin proteins must be expressed by the bacteria. If the invasin proteins are not expressed on the surface or not expressed at all, the Invaplex will not be present. For example, in S. sonnei one must use form I cultures because they are virulent. Form II cultures do not express the Ipa proteins due to a large spontaneous deletion in the virulence plasmid.

Ipa protein presentation on the surface of shigellae may be decreased by mutating genes in the spa or mxi gene loci. The spa/mxi gene mutants make the Ipa proteins in normal quantities but the Ipa proteins are not presented or secreted to the exterior of the organism. Previously it has been shown that reduced amounts of IpaB and IpaC are in the water extract in spa mutants (Venkatesan et al., 1992, J. Bacteriol. 174, 1990–2001)

To overcome the possibility of using avirulent cultures, it is important that cultures used as a source of Invaplex be tested and proven to be virulent. This is usually done by the Sereny test (keratoconjunctivitis in guinea pigs as described in the Materials and Methods and Examples below). Another means in which to assure virulence is growing cultures of shigellae on Congo Red media in which colonies that are red (or bind the dye congo red) are almost always virulent. Assessment of virulence is extremely important with shigellae cultures as spontaneous mutations leading to avirulent cultures is commonplace. It is understood that even though some cultures may be partially virulent, it is possible to isolate Invaplex though the yield will be compromised.

In one embodiment, this invention relates to a method for isolating and purifying the Invaplex from gram negative bacteria. The present method uses an improvement of the water extraction technique described by Oaks et al., 1986 (*Infect Immun* 53, 57–63). These improvements were designed to increase yield of functional product by minimizing the time to prepare the water extract preparation. The improvements include using an ion-exchange column capable of concentrating the Invaplex thereby eliminating the need to concentrate the water extract by time-consuming ultrafiltration step prior to loading onto the ion-exchange column. Ultrafiltration often took overnight to perform during which time proteolytic degradation might occur. The Ipa proteins are extremely labile and degrade rather quickly. Another improvement is the amount of water used to extract the proteins. The present method uses a volume of water which is 1/20 the volume of the medium used to grow the culture instead of a ratio of 1/10 used previously (Oaks et al., 1986, supra). For example if the shigellae are grown in 20 liters of medium than one would use 1 liter of water for the extraction. Other modifications include filtration of the water extract with a 0.45 or 0.22 um membrane both before and/or after ultracentifugation. This step will remove bacteria from the water extract material and make it less likely to contain viable bacteria. This step will be essential for any product to be used in human trials. Also the original procedure described in Oaks, 1986 (supra) used PMSF (phenylmethylsulfonyl fluroide) a very potent and dangerous protease inhibitor. This protease inhibitor is no longer used because it is toxic. To minimize degradation of the proteins in the complex the water extract is maintained on ice to minimize proteolytic degradation.

The present method includes the steps of collecting bacterial cells, extracting the cells in sterile water, separating and discarding membrane fragments from the water extract resulting in a solution containing the Invaplex, and isolating the Invaplex from the solution. Growing gram negative bacteria in culture is known to a person with ordinary skill in the art. For a general reference, please see *Manual of Methods for General Bacteriology,* 1981, Washington, D.C., P. Gephardt et al., eds. Media and conditions for growth are discussed for Shigella in detail in Materials and Methods below. After growth, the bacterial cells are extracted in sterile water, 20 mM Tris-HCl, normal saline (0.15M NaCl), or other buffers as long as the conditions allow binding of the Invaplex 24 and Invaplex 50 fractions to the desired column.

It is preferable to delete detergents in the extraction solution since detergents tend to form mixed micelles (micelles containing a variety of proteins) which may not behave in a consistent manner on the ion-exchange column. Detergents will also solubilize integral membrane proteins which may interfere with the Invaplex product. Finally, detergents may disrupt or denature the Invaplex and solubilize all of the individual components of the complex. Sterile water can be prepared by methods known in the art, for example, filtering through a 0.10, 0.22 or 0.45 micron filters. The concentration of bacterial cells to water is preferably $1\times10^7$ to about $2\times10^{12}$ cells per ml of water or buffer, more preferably between $1\times10^8$ to about $2\times10^{11}$.

Extraction time is preferably regulated since if it is too long, degradation of product may result, and too short will result in poor yield of product.

A protease inhibitor can be added, during the extraction step to aid in reducing the protein degradation of the final product. Examples of proteases which could be added include phenylmethylsulfonyl fluoride (PMSF). Other protease inhibitors are available such as serine protease inhibitors but they are usually somewhat toxic. If the Invaplex is to be administered to living cells, it would be preferable to delete the protease inhibitors or remove it from solution prior to administration due to the toxicity of the protease inhibitors. However, if the Invaplex is to be used for an ELISA reagent, the protease inhibitor could be left in the solution, in fact it would be preferable to have it in the solution.

Next, the cells and membrane fragments are removed from the solution by methods known in the art such as centrifugation, filtration, microfiltration, ultrafiltration, however, ultracentrifugation is preferable for removing the small membrane fragments before the solution is subjected to ion-exchange chromatography. Following extraction, the complex may be separated from the cellular debris by any technique suitable for separation of particles in complex mixtures. The complex may then be purified by anion or cation exchange chromatography or other isolation techniques which may include, but are not limited to, ammonium sulfate or ethanol precipitation, acid extraction, electrophoresis, isoelectric focusing, immunoadsorption, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography. Anion exchangers include diethylaminoethyl (DEAE) {—OCH2CH2N+H(CH2CH3)2}; quaternary aminoethyl (QAE){—OCH2CH2N+(C2H5)—CH2CHOH—CH3}; and quaternary ammonium (Q){—OCH2CHOH—CH3CHOH—CH2N+(CH3)C3}. Such functional groups are bound to various supports, each support varying in particle size, but also vary with respect to the support material. Examples of support material include:Monobeads, 10 um bead of hydrophilic polystyrene/divinylbenzene {i.e., Mono Q (Pharmacia, Uppsala, Sweden)}, Minibeads, 3 um bead of a hydrophilic polymer {i.e., Mini Q (Pharmacia)} SOURCE, 15 & 30 um monodispersed hydrophilized rigid, polystyrene/divinylbenzene beads {i.e., SOURCE Q (Pharmacia)} Sepharose, 34–50 um highly crosslinked agarose beads {i.e., HiTrap Q (Pharmacia) and Econo-Pac High Q (Bio-Rad)} Sepharose Fast Flow, 90 um agarose beads {i.e., QSepharose Fast Flow (Pharmacia)}, Sepharose Big Beads, 100–300 um agarose beads {i.e., QSepharose Big Beads (Pharmacia)}.

The chloride ion (Cl-) is the counterion of choice for anion exchange chromatography, with the choice of buffer dependent on the required pH interval. While Tris has a an effective buffering range of 7.6 to 8.0. Other buffers which may be used include: N-methyl-diethanolamine (pH 8.0–8.5), diethanolamine (pH 8.4–8.8), 1,3-diaminopropane (pH 8.5–9.0), ethanolamine (pH 9.0–9.5), and potentially piperazine (pH 9.5–9.8). These buffers are used at a low concentration, usually 20 mM, but could be as high as 50 mM.

Other columns or methods may be used as long as they maintain native structure of the Invaplex so that immunogenicity and function is intact, allow large volumes of a dilute protein solution to be loaded and concentrated, the buffers are biologically compatible, the method is rapid in order to minimize degradation of product and few processing steps are required.

It is preferable that each column be dedicated to a specific serotype and strain of gram-negative bacteria. The optimal protein concentration in the final product would be approximately 10 doses per ml. But the range could be as low as 0.1 dose per ml (protein conc. of 2.5 ug/ml) up to much higher levels of 5000 doses per ml (protein conc. of 125 mg/ml) as long as solubility is maintained, i.e. concentration not too high to cause precipitation and not too low to make filtration too costly and time consuming.

Ideally we are achieving 0.25 mg/ml to 5 mg/ml in peak fractions of Invaplex 24 and Invaplex 50. If protein concentration is less than 0.25 mg/ml than it must be concentrated by centrifugal size-exclusion filtration (mw cutoff of 10000 to 100,000 more preferably 30,000 mw cutoff).

Using the method described in the Materials and Methods below, the fractions containing the greatest amount of IpaB and IpaC were found in fractions eluted at 24% buffer and 50% buffer from the ion-exchange column, resulting in Invaplex 24, and Invaplex 50.

This method needs to be modified minimally for use with other gram-negative bacteria. For example, other ion-exchange columns can be used, and different antibodies must be used to probe for the target antigens. For example, antibodies for SipB and SipC would have to be used to identify peak fractions containing the complex from Salmonella. Yersinia would need anti YOP protein antibodies (Corneliz and Wolf-Watz, 1997, *Mol. Microbiol.* 23, 861–867).

Other methods for producing Invaplex include methods whereby individual subunit invasin proteins are combined with LPS in order to form a complex with a native configuration. In addition, the invasin/LPS complex can be further purified from other components in the Invaplex 24 and Invaplex 50 fractions by purification techniques as described above and below.

In another embodiment, the present invention relates to monoclonal or polyclonal antibodies specific for the above-described invasin complex. For instance, an antibody can be raised against a complex described above, or against a portion thereof of at least 10 amino acids, preferably, 11–15 amino acids. The peptides can be chosen to contain structural or conformational epitopes. Persons with ordinary skill in the art using standard methodology can raise monoclonal and polyclonal antibodies to an invasin complex or polypeptide chosen of the present invention, or a unique portion thereof. Material and methods for producing antibodies are well known in the art (see for example Goding, in, *Monoclonal Antibodies: Principles and Practice,* Chapter 4, 1986).

In a further embodiment, the present invention provides a method for detecting a gram-negative infection in a biological sample. By "biological sample" is intended any biological sample obtained from a subject. A subject is an insect, arthropod, animal, bird, fish, cell line, tissue culture, mammal including humans or other source, as well as other environmental samples such as water, plant, food, which may contain gram negative bacteria. Biological samples include body fluids (such as saliva, blood, plasma, urine, mucus, synovial fluid, stool etc.) tissues (such as muscle, skin, and cartilage) and any other biological source suspected of containing gram negative bacteria or the invasin complex of a gram negative bacteria. Methods for obtaining biological samples are known in the art.

Assaying for gram-negative bacteria infections can occur using any art-known method, such as antibody-based techniques. For example, the presence of Invaplex can be studies with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of invasin complex for Western-blot or dot/slot assay.

Other antibody-based methods useful for detecting gram negative infection include immunoassays, such as the ELISA and the radioimmunoassay (RIA). Using standard methodology well known in the art, a diagnostic assay can be constructed by coating on a surface (i.e. a solid support) for example, a microtitration plate, a membrane (e.g. nitrocellulose membrane), polymeric beads, or dip sticks, antibodies specific for invasin complex or invasin complex itself, or fragments thereof, and contacting it with a sample from a person suspected of having a gram negative bacterial infection. The presence of a resulting complex formed between invasin complex and antibodies specific therefor in the sample can be detected by any of the known detection methods common in the art such as fluorescent antibody spectroscopy or colorimetry. A good description of a radio-immune assay may be found in *Laboratory Techniques and Biochemistry in Molecular Biology.* by Work, T. S., et al. North Holland Publishing Company, N.Y. (1978), incorporated by reference herein. Sandwich assays are described by Wide at pages 199–206 of *Radioimmune Assay Method*, edited by Kirkham and Hunter, E. & S. Livingstone, Edinburgh, 1970. ELISA assays and other immunological methods included in the present invention can also be found in Harlow et al., *Antibodies: A Laboratory Manual,* Cold Spring Harbor Laboratory Press, 2nd ed., 1988.

Invaplex or anti-invaplex antibodies, or fragments of ligands or antibodies capable of detecting Invaplex may be labeled using any of a variety of labels and methods of labeling for use in diagnosis and prognosis of gram negative bacterial infection. Examples of types of labels which can be used in the present invention include, but are not limited to, enzyme labels, radioisotopic labels, non-radioactive isotopic labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{111}$In, $^{125}$I, $^{32}$P, $^{35}$S, $^{14}$C, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, $^{11}$C, $^{19}$F, $^{123}$I, etc.

Examples of suitable non-radioactive isotopic labels include $^{157}$Gd, $^{55}$Mn, $^{162}$Dy, $^{52}$Tr, $^{46}$Fe, etc.

Examples of suitable fluorescent labels include a $^{152}$Eu label, a fluorescein label, an isothiocyanate label, a rhodamine label, a phycoerythrin label, a phycodyanin label, an allophycocyanin label, a fluorescamine label, etc.

Examples of chemiluminescent labels include a luminal label, an isoluminal label, an aromatic acridinium ester label, an imidazole label, an acridinium salt label, an oxalate ester label, a luciferin label, a luciferase label, etc.

Those of ordinary skill in the art will know of other suitable labels which may be employed in accordance with the present invention. The binding of these labels to invasin complex, ligands or to antibodies or fragments thereof can be accomplished using standard techniques commonly known to those of ordinary skill in the art. Typical techniques are described by Kennedy, J. H., et al.,1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The detection of the antibodies (or fragments of antibodies) of the present invention can be improved through the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to Invaplex or Invaplex antibodies. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation.

The Invaplex and antibodies of the present invention, including fragments thereof may be used to detect gram-negative bacteria or gram-negative bacterial infection using bio chip and biosensor technology. Bio chip and biosensors of the present invention may comprise the polypeptides of the present invention to detect antibodies, which specifically recognize Invaplex. Bio chips or biosensors comprising polypeptides or antibodies of the present invention may be used to detect gram negative bacteria in biological and environmental samples and to diagnose an animal, including humans, with a gram negative bacterial infection. Thus, the present invention includes both bio chips and biosensors comprising polypeptides or antibodies of the present invention and methods of their use.

The Invaplex can be used to identify inhibitors of Invaplex. Natural and synthetic agents and drugs can be discovered which result in a reduction or elimination of the invasin complex. Knowledge of the mechanism of action of the inhibitor is not necessary as long as a dissociation of the complex is detected. Inhibitors may include agents or drugs which either bind or sequester the Invaplex. Agents or drugs related to this invention may result in partial or complete inhibition of virulence of gram negative bacteria, and possible inhibitors of Invaplex may be used in the treatment or amelioration of gram negative bacterial infections.

In providing a patient with agents which modulate the function of invasin complex to a recipient patient, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient) although a lower or higher dosage may be administered.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences* [16th ed., Osol, A. ed., Mack Easton, Pa. (1980)]. In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethacellulose or gelatin-microcapsules and poly (methylmethacrylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The present invention also provides kits for use in the diagnostic or therapeutic methods described above. Kits according to this aspect of the invention may comprise one or more containers, such as vials, tubes, ampules, bottles and the like, which may comprise one or more of the compositions of the invention.

The kits of the invention may comprise one or more of the following components, one or more compounds or compositions of the invention, and one or more excipient, diluent, or adjuvant.

One particularly important and significant advantage of the Invaplex 24 and Invaplex 50 is that, when used in an embodiment to modulate (i.e. regulate) the immune response, administration to an animal or an antigen-carrying Invaplex, or administration of Invaplex along with an antigen of interest, induces the animal to produce a cell-mediated as well as a humoral immune response against that antigen, without causing harmful side effects. Such a property has been much sought after without a great deal of success using killed microorganisms (e.g., bacteria or viruses), subunit vaccines, vaccines carried in viral or bacterial vehicles, and vaccines that include an adjuvant. An antigen refers to any compound heterologous to the Invaplex itself. The antigen is combined with the Invaplex by simply mixing the two substances together. However we fully anticipate making the Invaplex in the presence of the substance to be delivered but this would be more likely to be used for small molecules or pharmaceuticals not antigens.

The compound may be an organic or inorganic compound not found naturally in the gram-negative bacteria used in the production of the Invaplex, and/or a compound encoded by such a nucleic acid molecule (e.g., an RNA molecule or a protein). Organisms that can be protected from a disease are organisms that are susceptible to such a disease and preferably include animals and plants. Compounds can be carried while complexed to the Invaplex, inside, outside, or combinations thereof such that when the Invaplex is administered to an animal, it stimulates a desired immune response against the complexed compound. Any gram-negative invasive bacteria can be used to produce an Invaplex of the present invention.

Invaplex can be used as a vehicle, for the delivery of DNA, RNA, protein, or drug into a specific cell type that is interactive with the Invaplex. The Invaplex can be made in the presence of the substance to be delivered such as small molecules or pharmaceuticals. The stage that the Invaplex would be loaded with the compounds would be during the water extraction.

Described below are examples of the present invention which are provided only for illustrative purposes, and not to limit the scope of the present invention. Other suitable modifications and adaptations of the variety of conditions and parameters normally encountered in this art which are obvious to those skilled in the art are within the spirit and scope of the present invention.

The following methods and materials were used in the examples below.

Bacterial Growth and Strains. Most of the Shigella strains used in these studies are part of the WRAIR collection. They include *Shigella flexneri* 5 (M90T-W and Inc103, both are vir+), *S. flexneri* 5 (M90T-55, vir−), *S. flexneri* 2a (2457T), *S. sonnei* (Mosley), *S. dysenteriae* 1 (Ubon), and enteroinvasive *Escherichia coli* (0152). *S. boydii* 2 (CDC strain 3057–98) was kindly provided by N. Strockbine.

Isolated Shigella colonies were used to inoculate 50 mls of PenAssay (Antibiotic Medium #3, Difco) broth at 37° C. After 4 hrs of growth, 10 mls of the log phase culture were added to each liter of prewarmed (37° C.) PenAssay broth to be used for overnight growth. The 1 liter cultures were incubated overnight at 37° C. in a shaking incubator.

Water Extraction of Shigella proteins. A modification of the original water extraction procedure described by Oaks et al (Oaks et al, 1986, supra) was used to prepare the material from which the Shigella invasin complex was isolated. Identical procedures are used for enteroinvasive *E. coli*. Typically, four liters of an overnight culture of virulent shigellae were used for one batch of water extract. The bacterial cells were collected by centrifugation in a GS3 rotor (Sorvall), at 6000 rpm (apx 6000×g) for 30 min at 4° C. Next the bacterial cells were suspended in sterile, deionized water (0.45 um membrane filtered) at a volume of 50 mls per liter of overnight culture, and incubated at 37° C. in a shaking water bath (apx 200 rpm) for 2 hrs. After extraction with water, the cells were collected by centrifugation at 16000×g (GSA rotor, 10000 rpm) for 30 min at 4° C. The supernatant was collected and centrifuged at approximately 100,000×g for 1 hr at 4° C., to pellet membrane fragments. The 100,000×g supernatant was decanted into a sterile, pre-chilled flask, on ice. All 100,000×g supernatants for a single batch of water extract were pooled at this time. All samples were maintained on ice when possible and protease inhibitors were not used during the procedure. The water extract was stored at −70° C.

Characterization of Water Extract. The total protein content of each batch of water extract was measured by the bicichoninic acid assay (Pierce Chemical Company, Rockford, Ill.). Water extract batches were also analyzed for the presence of IpaB, IpaC and IpaD by western blots or spot blots using IpaB (mab 2F1), IpaC (mab 2G2), and IpaD (mab 16F8) specific monoclonal antibodies (Mills et al., 1988, *Infect. Immun.* 56, 2933–2941; Turbyfill et al, 1998, *Infect. Immun.* 66, 1999–2006) to probe for the individual Ipa proteins. Only water extracts which were positive for the Ipa proteins were used for invasin complex purification.

FPLC (Fast protein liquid chromatography). Ion exchange chromatography was used to isolate invasin complex fractions from the water extract. A 5 ml anion exchange HiTrapQ (Pharmacia, Uppsala, Sweden) column was equilibrated with 20 mM Tris-HCl, pH 9.0 (buffer A) at ambient temperature. Prior to loading, Tris-HCl (0.2 M, pH 9.0) was added to the water extract sample to a final concentration of 20 mM, after which 20 mls of the water extract was run through the column at a flow rate of 2 ml/min. After loading, the column was washed with 6 column volumes of buffer A. All elutions were carried out with step gradients consisting of 24% buffer B, followed by a 50% buffer B step, and finally the column was washed with 100% buffer B (1M NaCl in 20 mM Tris-HCl, pH 9.0). After washing with 100% buffer B, the column was reequilibrated with buffer A before the next run. Each column used in these studies was dedicated to a specific serotype and strain of Shigella. Protein passing through the column was monitored at 280 nm and 2 ml fractions were collected into polypropylene tubes. Data from the U.V. detector was recorded via the ADInstruments PowerChrom data acquisition and analysis software for the Macintosh computer operating system. Several FPLC runs were required for each water extract batch. As fractions were collected they were immediately placed at −70° C.

Each fraction was analyzed by immuno-spot blot for the presence of IpaC and IpaB. Fractions (usually 1 or 2) containing the greatest amount of IpaB & IpaC in the 24% buffer B were pooled as were peak Ipa protein fractions in the 50% buffer B step, resulting in Invaplex 24 and Invaplex 50 for a run. Invaplex 24 and Invaplex 50 run pools, once determined to be relatively similar with respect to IpaB, IpaC, & IpaD content (determined by western blot), LPS content (determined by silver stain analysis of gels, see below) and total protein composition, were combined for all runs from a particular batch of water extract. These final pools were aliquoted into 1.5 ml samples and stored at −80° C. and identified as a particular "lot" of Invaplex 24 or Invaplex 50.

ELISA using water extract, IpaC, LPS, and ovalbumin as antigens.

ELISA assays were used to measure antibody levels to various antigens in animal sera (Oaks et al, 1986, supra; Turbyfill et al, 1998, supra). Antigens used include water extract from vir+ (M90T-W) and vir− (M90T-55) strains of *S. flexneri* 5; purified LPS *S. flexneri* 2a, *S. flexneri* 5, *S. sonnei*, *S. dysentereiae* 1, *S. boydii* 2, and enteroinvasive *E. coli* 0152; and ovalbumin (Sigma Chemical Co.). Concentrations of antigen used in the assays were 1 ug/well (water extract, LPS, and ovalbumin) and 0.5 ug/well for purified IpaC and IpaD. Antigens were diluted in carbonate coating buffer (0.2 M carbonate, pH 9.8) and added to polystyrene 96-well antigen plates (Dynex Technologies, Inc, Chantilly, Va.). Next the antigen was removed from the wells followed by the addition of 2% casein (2% casein in a Tris-saline buffer, pH 7.5) to block the plates. Primary antibodies were diluted in 2% casein and were incubated with the antigen for 2 hrs. After 4 washes in PBS (10.75 mM sodium phosphate, 145 mM NaCl) with 0.05% Tween 20, plates were probed with commercial anti-immunoglobulin IgG or IgA (diluted 1/500 in casein, Kirkgaard & Perry, Gaithersburg, Md.) conjugated with alkaline phosphatase. The conjugates were diluted in the casein diluent. The substrate used in all ELISAs was para-nitrophenyl phosphate (1 mg/ml in 10% diethanolamine buffer, pH 9.8, containing 0.1 mg/ml $MgCl_2$ and 0.02% sodium azide). The optical density (O.D.) was measured at 405 nm on a Molecular Devices ELISA plate reader.

Electrophoresis and western blots. Polyacrylamide gel electrophoresis was used for the separation and analysis of Shigella polypeptides and lipopolysaccharide. Gels for western blots and coomassie blue staining consisted of 13% acrylamide cross-linked with $N_1N^1$-diallytartardiamide, whereas gels for silver staining were cross-linked with bis-acrylamide. Western blots were performed as previously described (Oaks, et al,1986, supra). Silver staining (Tsai and Reeves, 1982, *Anal. Biochem.* 119, 115–119) was used to stain LPS in samples treated with proteinase K prior to loading on gels (Hitchcock and Brown, 1983, *J. Bacteriol.* 154, 269–277). Antisera used in western blots included monoclonal antibodies to IpaB (2F1), IpaC (2G2) and IpaD (16F8) and monkey convalescent sera which contains antibodies to all Ipa proteins and VirG.

Immunogenicity of Invaplex 24 and Invaplex 50. Small animals (guinea pigs or mice) were immunized with Invaplex 24 and Invaplex 50 to determine the immunogenicity and safety of these structures.

The ability of the Invaplex fractions to promote an immune response in Balb/c mice was tested in groups of 5 mice. Each mouse was immunized intranasally with 5 ug of Invaplex 24 or Invaplex 50 on days 0, 14, and 28. Diluent buffer was used to immunize control animals. A total antigen volume of 25 ul was delivered in 5 to 6 small drops applied to the external nares with a micropipet. Blood was taken by tail bleed from all mice on days 0, 21, and 35.

Guinea pigs (4 to 5 per group) were immunized intranasally with 25 ug/dose of either Invaplex 24 or Invaplex 50. Diluent buffer (0.9% saline) was used to immunize control animals. The antigen was applied to the external nares with a micropipet in a total volume of 50 ul per nostril. Guinea pigs were immunized on days 0, day 14, and day 28. Guinea pigs were bled on day 0, day 28, day 42, and 2 weeks after challenge, from the lateral ear vein. Prior to intranasal immunization guinea pigs and mice were anesthetized with ketamine/rompun.

Challenge of guinea pigs immunized with with Invaplex 24 or Invaplex 50.

Three weeks after the 3rd immunization, guinea pigs were challenged intraocularly with *S. flexneri* 5 (M90T-W) (3.6×$10^8$ cfu), *S. flexneri* 2a (2457T (6.0×$10^8$ cfu), *S. sonnei* (Mosley) (4.1×$10^8$ cfu), *S. dysenteriae* 1 (4.8×$10^8$ cfu), *S. boydii* 2 (5.2×$10^8$ cfu), or enteroinvasive *E. coli* 0152 (5.8×$10^8$ cfu and observed daily for 5 days for the occurrence of keratoconjunctivitis. Scoring of the degree of inflammation and keratoconjunctivitis has been previously described (Hartman, et al.,1991, *Infect. Immun.* 59, 4075–4083).

Use of Invaplex 24 and Invaplex 50 as adjuvants. The ability of the Invaplex fractions to promote an immune response in Balb/c mice to an otherwise non-immunogenic molecule was assessed with ovalbumin, given intranasally. In addition, the ability to promote an immune response to purified LPS from a different species of Shigella (*S. sonnei*) was evaluated. Cholera toxin (CT, Berne Scientific, Miami, Fla.) was used as a positive adjuvant control. Groups of 5 mice were immunized intranasally with 5 ug of Invaplex 24, Invaplex 50, or CT adjuvants alone or mixed with 10 ug of ovalbumin or LPS. Intranasal immunization is an excellent site for stimulating both the secretory and humoral immune system. Control animals received intranasal doses (10 ug) of either ovalbumin or LPS alone. A total volume of 25 ul was used for immunization doses. Prior to intranasal immunization, mice were anesthesized with ketamine/rompun. The 25 ul dose was delivered in 5 to 6 small drops applied to the external nares with a micropipet. Mice were immunized on days 0, 14, and 28. Blood was taken by tail bleed from all mice on days 0, 21, and 35.

Invaplex as a Diagnostic Tool. Purified Invaplex 24 and Invaplex 50 were used in an ELISA to measure antibody levels in serum or body secretions such as saliva or tears. The presence of the invasin complex structure in this assay very likely maintains epitopes not normally found in purified or isolated components of the complex. By block titration it was determined that 0.05 ug/well of the Invaplex preparations was optimal for high sensitivity and low background. Therefore in the ELISA, polystyrene antigen plates (Dynex Technologies, Inc., Chantilly, Va.) were coated with either Invaplex 24 or Invaplex 50 diluted in carbonate buffer (pH 9.8), at a final concentration of 0.05 ug/well. After blocking with 2% casein, pre- and post-infection monkey sera (diluted ¹⁄₄₀₀ and ¹⁄₁₆₀₀) were incubated for 2 hrs with the antigen coated plates, followed by 4 washes in PBS-Tween 20. Bound primary antibody was detected with goat anti-human IgG conjugated with alkaline phosphatase (1 hr, ¹⁄₅₀₀ dilution). After washing with PBS-tween 20 as described above, the substrate, para-nitrophenyl phosphate (1 mg/ml in diethanolamine), was added and incubated for 30 min. Optical density was measured at 405 nm in Molecular Devices ELISA reader.

The monkey sera used in these studies were from the WRAIR collection. The monkeys were infected with *S. flexneri* 2a in studies M218 and M219. In the study SC602 animals were first immunized with the living attenuated vaccine SC602, which is an icsA/iuc double mutant of *S. flexneri* 2a (Barzu et al., 1998, *Infect. Immun.* 66, 77–82) and subsequently challenged with *S. flexneri* 2a. Control animals in the SC602 vaccine trial were treated only with bicarbonate buffer and then challenged with virulent *S. flexneri* 2a (2457T). In all monkey studies blood was collected 2 weeks post challenge or post-vaccination.

EXAMPLE 1

Isolation and Characterization of Invaplex 24 and Invaplex 50

In initial experiments, the water extracted material was eluted from an FPLC ion-exchange column with continuous 0 to 1.0 M NaCl gradients in 20 mM Tris, pH 9.0. It was found that the majority of the IpaB and IpaC proteins consistently eluted in two peaks at approximately 24% buffer B and 50% buffer B (data not shown). Therefore, step gradients of 24% buffer B., 50% buffer B, and a final wash at 100% buffer B were used in all subsequent elutions.

Typical chromatographs for water extracts from *S. flexneri* 5, *S. flexneri* 2a, *S. sonnei*, *S. dysenteriae* 1, *S. boydii* 2, and enteroinvasive *E. coli* 0152 separated by FPLC into the invasin complex peaks are in FIGS. 2(A–F). The Invaplex 24 peak and Invaplex 50 peak are labeled for each chromatograph. Peak 0 (zero % buffer B) represents protein that did not bind to the HiTrapQ anion-exchange column. A 100% buffer B peak (peak 100) is also indicated. Each fraction was evaluated by spot blot with IpaB and IpaC Mabs. The fractions containing most of the IpaB and IpaC activity were in the Invaplex 24 and Invaplex 50 peaks. This FPLC profile is reproducible in that identical results are obtained with the same batches of water extract, with different batches of water extract, and with water extracts from all four species of Shigella as well as enteroinvasive *E. coli* (see FIGS. 2(A–F)). Typical yields of Invaplex 24 and Invaplex 50 are approximately 5 mg and 1 mg, respectively, per liter of original culture.

Figure 3:
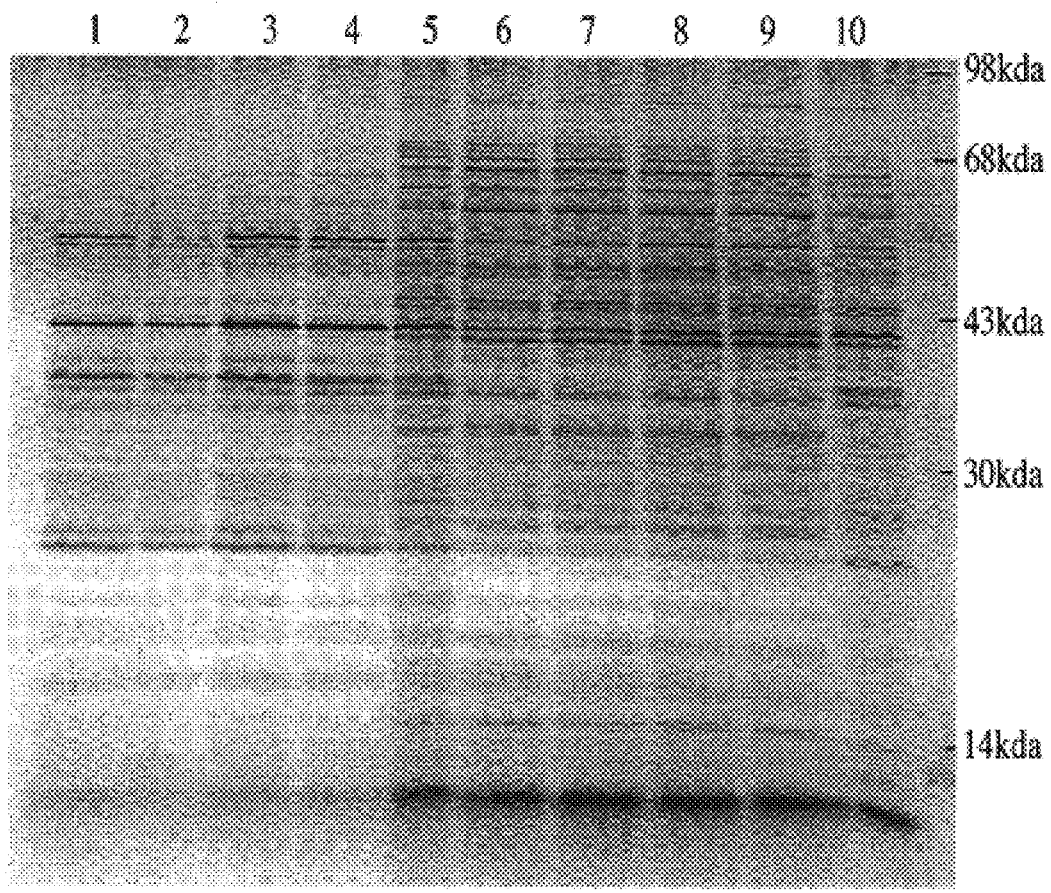
FIG. 3. Silver stain analysis of polyacrylamide gel electrophoresis separated *S. flexneri* 2a Invaplex 24 and Invaplex 50 samples collected from different FPLC purification runs. *S. flexneri* 2a Invaplex 24 and Invaplex 50 from four different purification runs are in lanes 1, 2, 3, 4, and lanes 6, 7, 8, 9, respectively. Other samples include water extract from *S. flexneri* 2a, strain 2457T (lanes 5 and 10). Molecular weight standards are indicated to the right of the figure. The four Invaplex 24 and the four Invaplex 50 samples are remarkedly consistent, both qualitatively and quantitatively.

The consistency of different FPLC runs of purified Invaplex 24 or Invaplex 50 was evalauated by western blots and by silver stained polyacrylamide gels (FIG. 3). The silver stained gels confirm the overall consistency of each FPLC run. It was also possible to show that the same antigenic composition (for example the presence of IpaB, IpaC, IpaD) was present in Invaplex 24 or Invaplex 50 preparations purified at different times (data not shown). Each Invaplex 24 preparation is identical as are each of the Invaplex 50 preparations.

Figures 4A, 4B:
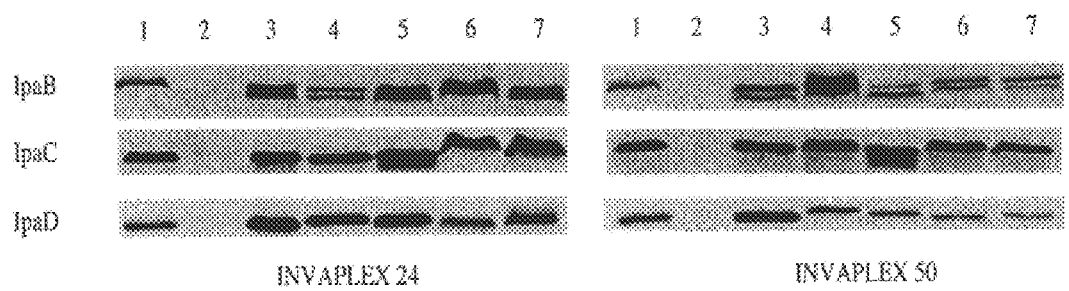
FIG. 4. Western blot analysis of Invaplex 24 and Invaplex 50 from *S. flexneri* 2a, *S. sonnei*, *S. dysenteriae* 1, *S. boydii* 2, and enteroinvasive *E. coli* 0152 with monoclonal antibodies against IpaB, IpaC and IpaD. Samples run on this gel are, whole-cell lysates of *S. flexneri* 5, M90T-Wash, vir+ (lane 1), whole-cell lysates of *S. flexneri* 5, M90T-55, vir− (lane 2), and Invaplex 24 (left panel) or Invaplex 50 (right panel) from *S. flexneri* 2a (lane 3), *S. sonnei* (lane 4), *S. dysenteriae* 1 (lane 5), *S. boydii* 2 (lane 6), and enteroinvasive *E. coli* 0152 (lane 7). This is a composite of western blots probed with monoclonal antibodies reactive with IpaB (Mab 2F1), IpaC, (Mab 2G2) and IpaD (Mab 16F8). The IpaB, IpaC and IpaD bands are noted. Each lane containing Invaplex preparations was loaded with 20 ug protein.

Invaplex preparations from different Shigella serotypes were also evaluated and compared to determine if the Invaplex composition varied from one species to another. FIG. 4 is a composite of several western blots of Invaplex 24 and Invaplex 50 preparations probed for different antigens with monoclonal antibodies against IpaB, IpaC and IpaD (FIG. 4). The Invaplex 24 and Invaplex 50 preparations from *S. flexneri* 5, *S. flexneri* 2a, *S. sonnei*, *S. dysenteriae*, *S. boydii* and enteroinvasive *E. coli* all contained IpaB, IpaC, and IpaD. Both Invaplex 24 and Invaplex 50 also contained IpaA. One difference between the Invaplex 24 and Invaplex 50 preparations is that Invaplex 24 samples contain relatively more IpaD than do the Invaplex 50 preparations (see FIG. 4 and Table 1). In addition, the Invaplex 50 preparations contain VirG* (a truncated form of the 120 kdal VirG* protein). VirG* has not been detected in Invaplex 24 fractions by the methods used. Additional proteins are present in the Invaplex preparations but their identities are not known (Formal, et al., 1991, *J. Infect. Dis.* 174, 533–537; Lett et al., 1989, *J. Bacteriol.* 171, 353–359).

TABLE 1A

Summary of Antigen Content in Invaplex 24
Preparations Based on Western Blot Analysis or
Silver Stained Polyacrylamide Gels

| | IpaD[1] | IpaB[1] | IpaC[1] | LPS[2] | IpaA[1] | VirG*[1] |
|---|---|---|---|---|---|---|
| *S. flexneri* 2a | ++[3] | ++ | ++ | + | + | − |
| *S. sonnei* | ++ | + | ++ | +/− | + | − |
| *S. boydii* 2 | + | ++ | ++ | + | + | − |
| *S. dysenteriae* 1 | ++ | ++ | ++ | + | + | − |
| EIEC[4] | +/− | ++ | ++ | + | + | + |

TABLE 1B

Summary of Antigen Content in Invaplex 50
Preparations Based on Western Blot Analysis or
Silver Stained Polyacrylamide Gels

| | IpaD[1] | IpaB[1] | IpaC[1] | LPS[2] | IpaA[1] | VirG*[1] |
|---|---|---|---|---|---|---|
| *S. flexneri* 2a | ++[3] | + | ++ | + | + | ++ |
| *S. sonnei* | + | ++ | ++ | + | + | ++ |
| *S. boydii* 2 | + | + | ++ | + | + | ++ |

TABLE 1B-continued

Summary of Antigen Content in Invaplex 50
Preparations Based on Western Blot Analysis or
Silver Stained Polyacrylamide Gels

| | IpaD[1] | IpaB[1] | IpaC[1] | LPS[2] | IpaA[1] | VirG*[1] |
|---|---|---|---|---|---|---|
| S. dysenteriae 1 | + | + | ++ | + | + | ++ |
| EIEC[4] | + | + | ++ | + | + | ++ |

[1]These results are based on western blots using monoclonal sera against IpaD, IpaB, and IpaC, or monkey convalescent sera which contains antibodies agaisnt all Ipa proteins and also VirG (and VirG*, a truncated form of VirG)
[2]LPS was detected in proteinase K treated samples run on polyacrylamide gels stained with silver
[3]Scoring is graded as follows: "++" indicates a strongly positive reaction on the western blot; "+" is a positive reaction; "+/−" is a weak reaction; and "−" is a negative reaction.
[4]EIEC = enteroinvasive E. coli.

Figure 5A:
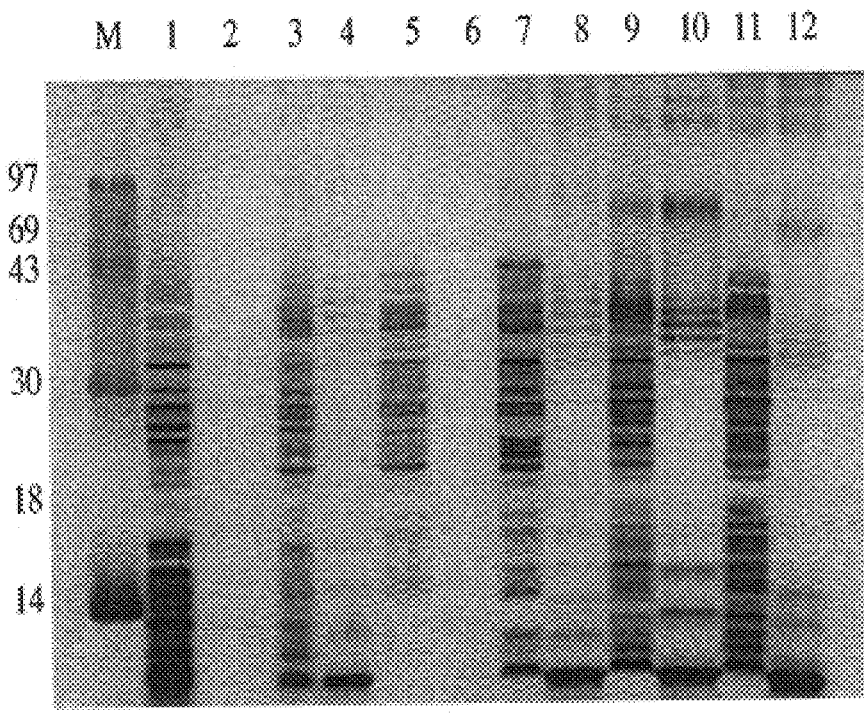
FIGS. 5(A,B). Analysis of Invaplex 24 and Invaplex 50 for the presence of LPS by silver staining of electrophoresed samples that were treated with proteinase K (PK). Proteinase K-digested and undigested preparations of Invaplex 24 (FIG. 5A) and Invaplex 50 (FIG. 5B) from each species of Shigella or EIEC were analyzed. A. Samples on gel A are molecular weight standards (M); *S. flexneri* 5, M90T-W, Vir+, whole cell lysate (lane 1); electrophoresis sample buffer (lane 2); Invaplex 24 from *S. flexneri* 2a undigested (lane 3) and digested (lane 4); Invaplex 24 from *S. sonnei* Mosley undigested (lane 5) and digested (lane 6); Invaplex 24 from *S. dysenteriae* 1 undigested (lane 7) and digested (lane 8); Invaplex 24 from *S. boydii* 2, undigested (lane 9) and digested (lane 10); and Invaplex 24 from enteroinvasive *E. coli* O152, undigested (lane 11) and digested (lane 12). B. Samples on gel B are identical to those in panel A except that the Invaplex samples are Invaplex 50 preparations from the different Shigella and *E. coli* strains. Bands remaining after PK treatment are LPS bands which run from the very small molecular-sized core (at the bottom of the gel) to the larger forms of LPS containing the species-specific, O-side chains.
Figure 5B:
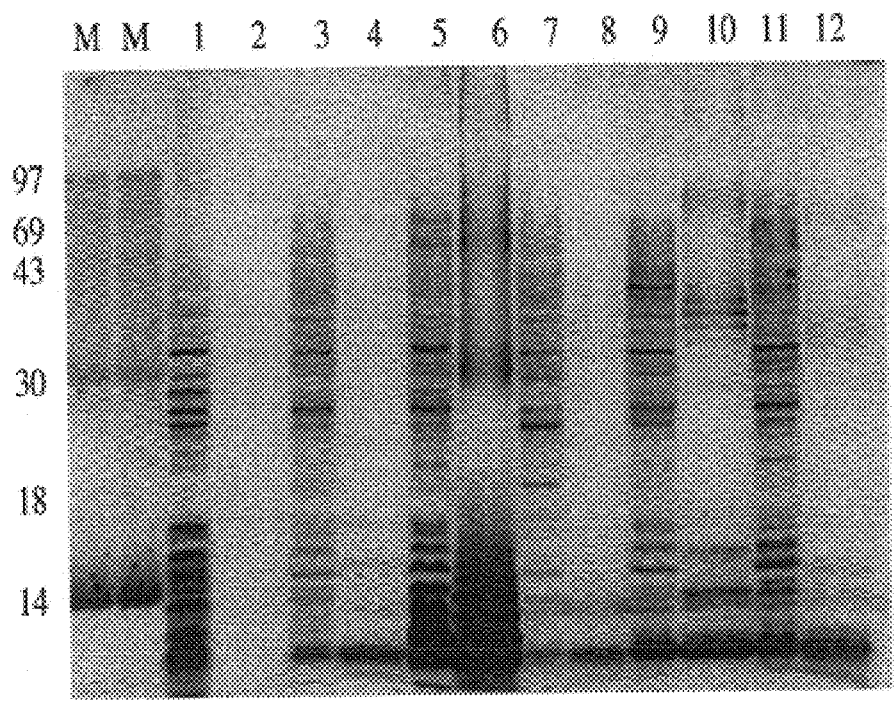

Lipopolysaccharide can be detected by silver staining polyacrylamide gels. If samples are treated first with proteinase K to digest all proteins, then only the LPS will be present in the samples. FIGS. 5(A,B) shows silver stained gels of Invaplex 24 and Invaplex 50 preparations from all Shigella spp and enteroinvasive E. coli before and after proteinase K treatment. A typical LPS core (a prominant band at the bottom of the gel) was found in both Invaplex 24 and Invaplex 50 samples. In addition, other LPS bands at gradually increasing molecular sizes (representing varying degrees of biosynthesis of the O-side chains onto the core) were also present. Similar LPS profiles were present in Invaplex 24 and Invaplex 50 preparations from S. flexneri, S. boydii, S. dysenteriae and enteroinvasive E. coli. The LPS content of Invaplex 24 from S. sonnei was lower than that of other Invaplex preparations. Invaplex 50 from S. sonnei was similar to that of other Invaplex 50 preparations.

A summary of the various antigenic proteins and LPS in the Invaplex 24 and Invaplex 50 preparations for each species are in Table 1.

EXAMPLE 2
Immunogenicity and Safety of Invaplex 24 and Invaplex 50

Small animals (guinea pigs and mice) were immunized with Invaplex 24 or Invaplex 50 to determine the immunogenicity and safety of these structures and the individual components within the Invaplex preparations.

Mice immunized with the Invaplex 24 and Invaplex 50 preparations from S. flexneri 5 showed a marked serum IgA and IgG response to water extract antigen and LPS (see Table 2A and 2B). Serum antibodies to LPS and water extract were detected at low levels after 2 intranasal immunizations, but a more pronounced titer was achieved with 3 immunizations. Invaplex 50 immunization resulted in IgA and IgG antibodies against S. flexneri 5 LPS and the water extract antigen from both virulent and avirulent S. flexneri 5. Immunization with Invaplex 24 resulted in antibodies against LPS (at a lower titer than that generated with Invaplex 50) and a strong virulent specific response as detected by strong reactivity with the vir+ water extract antigen and minimal reactivity with the vir− water extract antigen. These data clearly show that the Invaplex preparations are highly immunogenic and do not require an adjuvant to generate an immune response. Both preparations stimulated both an IgA and IgG response. In addition these data indicate that the Invaplex 24 and Invaplex 50 are different in the specificity of the immune response they elicit.

Guinea pigs immunized with Invaplex 24 or Invaplex 50 prepared from each of the four Shigella species and EIEC responded with increased serum antibodies to several different Shigella antigens (see Table 3 and 4). The guinea pigs were immunized with 3, 25 ug doses administered intranasally every two weeks.

Invaplex 24 immunized guinea pigs produced a strong IgG response to LPS after three intranasal immunizations (table 3A). IgA to LPS was also produced after immunization with Invaplex 24 (Table 3B). Unlike the other Invaplex 24 preparations, animals immunized with S. sonnei Invaplex 24 produced a minimal titer against LPS. This supports data shown above that the Invaplex 24 from S. sonnei has less LPS than Invaplex 24 preparations from other Shigella spp. Even so, upon challenge with virulent S. sonnei, the S. sonnei Invaplex 24 animals produced a strong IgG and IgA response to LPS indicating that the immune system had been primed for an anti-LPS immune response by vaccination with Invaplex 24.

As evident in mice Invaplex 24 preparations stimulated a strong reaction with the vir+ water extract antigen and only a minimal response to the vir− water extract antigen (Table 3C and 3D). This is very similar to the virulent -specific immune response generated after infection with shigellae in humans or monkeys. Invaplex 24 preparations from all Shigella species tested stimulated a serum IgG response in guinea pigs. Upon challenge, the animals all showed a tremendous boost in antibody levels to the water extract indicating a successful priming by the Invaplex 24 vaccine. The boost in antibody levels was much higher than control animals treated with buffer and then challenged with shigellae.

Sera from guinea pigs immunized with Invaplex 24 were also measured for antibodies against the homologous Invaplex 24 and Invaplex 50 antigens used for vaccination. Thus if a group of animals were immunized with S. flexneri Invaplex 24, ELISAs were performed using S. flexneri Invaplex 24 and S. flexneri Invaplex 50 (see tables 3E and 3F). As expected the guinea pigs responded by producing antibodies to the immunizing Invaplex antigen. In most groups the antibody levels were greater for the identical Invaplex 24 antigen than for the Invaplex 50 antigen prepared from the same Shigella serotype. This provides further evidence that the Invaplex 24 and Invaplex 50 preparations are not identical. As seen before the S. sonnei Invaplex 24 immunized animals did not produce high levels of antibody after 3 immunizations but upon challenge with virulent S. sonnei they were able to mount an impressive memory response, again indicating that the Invaplex vaccine provides ample stimulus for the immune system.

EXAMPLE 3

Guinea pigs immunized with Invaplex 50 had strong antibody responses against water extract antigens (both vir+ and vir−) and LPS (Tables 4A–4F). The LPS responses elicited by Invaplex 50 vaccines (Table 4A and 4B) appeared comparable to that generated by the Invaplex 24 vaccine. Each group (except the S. dysenteriae Invaplex 50) produced anti-LPS IgG and IgA antibodies after 3 doses. Interestingly, animals immunized with the S. sonnei Invaplex 50 or the EIEC Invaplex 50 produced detectable IgG and IgA against LPS after just two immunization doses. Guinea pigs immunized with the S. dysenteriae Invaplex 50 produced minimal antibody levels against LPS however, upon challenge these animals did produce a dramatic increase in anti-LPS IgG, indicating that the Invaplex 50 vaccine was successful in priming these animal's immune system.

Invaplex 50 for all preparations from the different Shigella species and EIEC elicited a strong serum IgG response reactive with the water extract antigen (Tables 4C and 4D). Measureable IgG antibodies were present in each Invaplex 50 group after two doses of vaccine. This is somewhat better than that seen with the Invaplex 24 vaccines. Another difference is that the Invaplex 50 vaccines stimulated antibodies that were reactive with the water extract from a vir-shigellae. This is very likely due to antibodies being produced to non-plasmid encoded proteins which are present in the Invaplex 50 vaccine and not present or in low concentrations in the Invaplex 24 vaccine. Even so when the sera from Invaplex 50 immunized animals are analyzed by western blots, it is clear that antibodies to IpaC and IpaB are present. Thus, even though the immune response elicited by the Invaplex 50 vaccine doesn't appear to be virulent specific by the water extract ELISA (like that seen with Invaplex 24 or a natural infection) it does stimulate the production of antibodies to virulence proteins.

Sera from the Invaplex 50 immunized animals were also tested in ELISAs using Invaplex 50 or Invaplex 24 as the ELISA antigen (Table 4E and 4F). As seen with the Invaplex 24 vaccine, Invaplex 50 immunized animals produced high levels of IgG antibodies reactive with the immunizing Invaplex 50 antigen. Antibodies were detected after just two doses for all serotypes. Also a positive response was found against the Invaplex 24 antigen, but for the most part the antibody levels were lower than that measured by the Invaplex 50 antigen. Again, this is evidence that the Invaplex 50 and Invaplex 24 contain different antigens and stimulate antibodies with somewhat different specificities.

In all of the guinea pig experiments, control animals immunized with buffer diluent did not produce antibodies to any of the Shigella antigens tested. Upon challenge these animals produced much lower levels of antibodies than did those animals immunized with Invaplex 24 or Invaplex 50 vaccines.

TABLE 2

Immune Response to LPS and Water Extract in Mice Immunized with Invaplex 24 or Invaplex 50 from *S. flexneri* 5

| | LPS | | Water Extract Vir+ | | Water Extract Vir− | |
|---|---|---|---|---|---|---|
| Day | IgA | IgG | IgA | IgG | IgA | IgG |
| A. Immune Response in Mice Immunized with Invaplex 24 from *S. flexneri* 5 | | | | | | |
| 0 | .036 ± .001 | .030 ± .004 | .032 ± .001 | .020 ± .001 | .038 ± .002 | .022 ± .001 |
| 28 | .045 ± .009 | .047 ± .011 | .139 ± .007 | .124 ± .009 | .040 ± .005 | .043 ± .014 |
| 42 | .194 ± .145 | .189 ± .121 | .535 ± .095 | .761 ± .144 | .099 ± .05 | .136 ± .051 |
| B. Immune Response in Mice Immunized with Invaplex 50 from *S. flexneri* 5 | | | | | | |
| 0 | .036 ± .002 | .031 ± .004 | .043 ± .001 | .021 ± .001 | .046 ± .001 | .023 ± .001 |
| 28 | .092 ± .041 | .112 ± .053 | .059 ± .007 | .075 ± .011 | .078 ± .013 | .130 ± .027 |
| 42 | 1.239 ± .451 | 1.106 ± .333 | .495 ± .17 | .403 ± .082 | .717 ± .208 | .600 ± .111 |

Groups of 5 mice were immunized intranasally three times with *S. flexneri* 5 derived Invaplex (Invaplex 24 or Invaplex 50) The serum IgA or IgG reactive with *Shigella flexneri* 5 LPS and water extract (vir+ or vir−) was determined by ELISA. Blood was taken from all mice at 3 different time points; pre-treatment (day 0), post-2nd immunization (day 28), and after 3 immunizations (day 42). The values for each timepoint represent the mean $O.D._{405}$ ± S.E.M. for each group of 5 mice. Data from mice immunized with Invaplex 24 or Invaplex 50 are in panels A and B, respectively. In these experiments sera were diluted 1/180 for IgA analysis and 1/360 for IgG analysis.

TABLE 3

Serum Immune Response to Select Antigens in Guinea Pigs Immunized with Invaplex 24

| DAY | *S. flexneri* 2a | *S. flexneri* 5 | *S. sonnei* | *S. dysenteriae* | *S. boydii* | EIEC |
|---|---|---|---|---|---|---|
| A. Serum IgG antibody response to homologous LPS in guinea pigs immunized with Invaplex 24 from different *Shigella* species or EIEC | | | | | | |
| 0 | .021 ± .001 | .023 ± .002 | .023 ± .001 | .023 ± .001 | .033 ± .006 | .057 ± .005 |
| 28 | .083 ± .033 | .093 ± .065 | .026 ± .001 | .025 ± .002 | .043 ± .009 | .074 ± .012 |
| 42 | 1.129 ± .366 | .607 ± .352 | .034 ± .007 | .333 ± .246 | .042 ± .004 | .216 ± .092 |
| 56 | 2.976 ± .079 | 2.567 ± .4 | .621 ± .363 | 2.039 ± .508 | .111 ± .048 | .352 ± .135 |
| Control 0 | .021 ± .002 | .024 ± .002 | .024 ± .001 | .022 ± .0004 | .050 ± .006 | .039 ± .005 |
| Control 56 | .023 ± .001 | .477 ± .163 | .042 ± .009 | .023 ± .001 | .053 ± .009 | .066 ± .009 |
| B. Serum IgA antibody response to homologous LPS in guinea pigs immunized with Invaplex 24 from different *Shigella* species or EIEC | | | | | | |
| 0 | Not Done | Not Done | .038 ± .001 | .025 ± .001 | .024 ± .001 | .069 ± .004 |
| 28 | Not Done | Not Done | .041 ± .002 | .029 ± .003 | .034 ± .009 | .109 ± .023 |
| 42 | Not Done | Not Done | .072 ± .017 | .111 ± .061 | .042 ± ..007 | .162 ± .041 |
| 56 | Not Done | Not Done | 1.086 ± .192 | .383 ± .114 | .349 ± .103 | .310 ± .097 |
| Control 0 | Not Done | Not Done | .034 ± .001 | .025 ± .001 | .023 ± .001 | .088 ± .005 |
| Control 56 | Not Done | Not Done | .165 ± .056 | .035 ± .004 | .035 ± .003 | .132 ± .007 |
| C. Serum IgG antibody response to Water Extract Antigen (Vir+) in guinea pigs immunized with Invaplex 24 from different *Shigella* species or EIEC | | | | | | |

TABLE 3-continued

Serum Immune Response to Select Antigens in Guinea Pigs Immunized with Invaplex 24

| DAY | S. flexneri 2a | S. flexneri 5 | S. sonnei | S. dysenteriae | S. boydii | EIEC |
|---|---|---|---|---|---|---|
| 0 | .041 ± .010 | .048 ± .007 | .077 ± .017 | .045 ± .007 | .063 ± .012 | .069 ± .005 |
| 28 | .850 ± .303 | .047 ± .008 | .072 ± .004 | .061 ± .024 | .098 ± .017 | .191 ± .111 |
| 42 | 1.984 ± .182 | .194 ± .074 | .116 ± .022 | .713 ± .142 | .471 ± .180 | 1.240 ± .439 |
| 56 | 2.985 ± .035 | 1.807 ± .283 | .366 ± .190 | 1.742 ± .613 | .688 ± .268 | 1.426 ± .588 |
| Control 0 | .036 ± .006 | .052 ± .017 | .091 ± .019 | .056 ± .006 | .078 ± .004 | .077 ± .009 |
| Control 56 | .377 ± .131 | .93 ± .204 | .072 ± .017 | .135 ± .075 | .048 ± .017 | .059 ± .016 |

D. Serum IgG antibody response to Water Extract Antigen (Vir−) in Gguinea pigs immunized with Invaplex 24 from different *Shigella* species or EIEC

| DAY | S. flexneri 2a | S. flexneri 5 | S. sonnei | S. dysenteriae | S. boydii | EIEC |
|---|---|---|---|---|---|---|
| 0 | .069 ± .027 | .044 ± .009 | .074 ± .015 | .046 ± .003 | .061 ± .011 | .074 ± .012 |
| 28 | .073 ± .007 | .047 ± .01 | .066 ± .022 | .045 ± .005 | .075 ± .007 | .083 ± .007 |
| 42 | .072 ± .016 | .22 ± .155 | .117 ± .014 | .073 ± .011 | .097 ± .013 | .189 ± .029 |
| 56 | .331 ± .116 | 1.851 ± .387 | .679 ± .256 | .280 ± .034 | .129 ± .041 | .169 ± .037 |
| Control 0 | .037 ± .003 | .036 ± .006 | .062 ± .009 | .043 ± .004 | .059 ± .002 | .086 ± .013 |
| Control 56 | .247 ± .080 | .406 ± .051 | .078 ± .021 | .169 ± .117 | .041 ± .012 | .060 ± .016 |

E. Serum IgG antibody response to Invaplex 24 in guinea pigs immunized with Invaplex 24 from different *Shigella* species or EIEC

| DAY | S. flexneri 2a | S. flexneri 5 | S. sonnei | S. dysenteriae | S. boydii | EIEC |
|---|---|---|---|---|---|---|
| 0 | .042 ± .004 | Not Done | .034 ± .003 | .049 ± .003 | .025 ± .001 | .021 ± .001 |
| 28 | .259 ± .108 | Not Done | .040 ± .002 | .072 ± .020 | .042 ± .007 | .020 ± .001 |
| 42 | .808 ± .281 | Not Done | .047 ± .008 | .506 ± .075 | .260 ± .103 | .020 ± .001 |
| 56 | 3.269 ± .038 | Not Done | .140 ± .037 | 1.539 ± .406 | 1.097 ± .369 | .959 ± .371 |
| Control 0 | .067 ± .014 | Not Done | .037 ± .003 | .039 ± .003 | .055 ± .010 | .036 ± .002 |
| Control 56 | .216 ± .071 | Not Done | .046 ± .004 | .066 ± .017 | .084 ± .020 | .061 ± .005 |

F. Serum IgG antibody response to Invaplex 50 in guinea pigs immunized with Invaplex 24 from different *Shigella* species or EIEC

| DAY | S. flexneri 2a | S. flexneri 5 | S. sonnei | S. dysenteriae | S. boydii | EIEC |
|---|---|---|---|---|---|---|
| 0 | .044 ± .006 | Not Done | .043 ± .004 | .047 ± .012 | .037 ± .005 | .022 ± .001 |
| 28 | .132 ± .052 | Not Done | .035 ± .002 | .069 ± .024 | .044 ± .002 | .022 ± .001 |
| 42 | .404 ± .146 | Not Done | .057 ± .009 | .223 ± .057 | .101 ± .022 | .023 ± .001 |
| 56 | 2.462 ± .261 | Not Done | .424 ± .122 | .909 ± .299 | .806 ± .213 | .678 ± .278 |
| Control 0 | .049 ± .003 | Not Done | .042 ± .003 | .053 ± .004 | .040 ± .004 | .034 ± .004 |
| Control 56 | .751 ± .107 | Not Done | .100 ± .010 | .155 ± .020 | .066 ± .012 | .073 ± .018 |

TABLE 3. Serum Immune Response to Select Antigens in Guinea Pigs Immunized with Invaplex 24
Different groups of 5 guinea pigs were immunized intranasally on days 0, 14, and 28 with Invaplex 24 prepared from either *S. flexneri* 2a, *S. flexneri* 5, *S. sonnei*, *S dysenteriae*, *S. boydii* 2, or enteroinvasive *E. coli* (EIEC). The Invaplex source is listed at the top of each column. Antigens used in the ELISAs included LPS (TABLE 3A and 3B) prepared from the homologous *Shigella* serotype from which the Invaplex vaccine was prepared; water extract (TABLE 3C and 3D) was from *S. flexneri* 5 vir+ and vir−; and Invaplex 24 (TABLE 3E) and Invaplex 50 (TABLE 3F) were prepared from the same serotype from which the immunizing Invaplex was prepared. The serum IgG levels were measured for each of these antigens by ELISA. The serum IgA levels were solely determined for LPS. Blood was taken from all guinea pigs at 4 different time points, pre-treatment (day 0), post-2nd immunization (day 28), after 3 immunizations (day 42) and 1 week post-challenge (day 56). Animals were challenged with the same *Shigella* serotype from which the Invaplex vaccine was derived. The values for each time-point represents the mean $O.D._{405}$ ± S.E.M. for each group of 5 guinea pigs.

TABLE 4

Serum Immune Response to Select Antigens in Guinea Pigs Immunized with Invaplex 50

| DAY | S. flexneri 2a | S. flexneri 5 | S. sonnei | S. dysenteriae | S. boydii | EIEC |
|---|---|---|---|---|---|---|

A. Serum IgG antibody response to homologous LPS in guinea pigs immunized with Invaplex 50 from different *Shigella* species or EIEC

| DAY | S. flexneri 2a | S. flexneri 5 | S. sonnei | S. dysenteriae | S. boydii | EIEC |
|---|---|---|---|---|---|---|
| 0 | .023 ± .001 | .035 ± .01 | .024 ± .0002 | .023 ± .0004 | .047 ± .004 | .066 ± .009 |
| 28 | .025 ± .004 | 0.054 ± .009 | .024 ± .0002 | .023 ± .001 | .057 ± .014 | .168 ± .056 |
| 42 | .278 ± .104 | .913 ± .229 | 1.347 ± .296 | .039 ± .013 | .374 ± .200 | .736 ± .207 |
| 56 | .813 ± .189 | 2.931 ± .283 | 2.451 ± .286 | .592 ± .301 | .559 ± .272 | .916 ± .291 |
| Control 0 | .021 ± .002 | .024 ± .002 | .024 ± .001 | .022 ± .0004 | .050 ± .006 | .039 ± .005 |
| Control 56 | .023 ± .001 | .477 ± .163 | .042 ± .009 | .023 ± .001 | .053 ± .009 | .066 ± .009 |

B. Serum IgA antibody response to homologous LPS in guinea pigs immunized with Invaplex 50 from different *Shigella* species or EIEC

| DAY | S. flexneri 2a | S. flexneri 5 | S. sonnei | S. dysenteriae | S. boydii | EIEC |
|---|---|---|---|---|---|---|
| 0 | Not Done | Not Done | .037 ± .001 | .024 ± .001 | .023 ± .001 | .120 ± .02 |
| 28 | Not Done | Not Done | .142 ± .026 | .025 ± .002 | .071 ± .024 | .287 ± .079 |
| 42 | Not Done | Not Done | .183 ± .025 | .161 ± .129 | .179 ± .059 | .437 ± .101 |
| 56 | Not Done | Not Done | .567 ± .095 | .296 ± .139 | .535 ± .046 | .403 ± .055 |
| Control 0 | Not Done | Not Done | .034 ± .001 | .025 ± .001 | .023 ± .001 | .088 ± .005 |

TABLE 4-continued

Serum Immune Response to Select Antigens in Guinea Pigs Immunized with Invaplex 50

| DAY | S. flexneri 2a | S. flexneri 5 | S. sonnei | S. dysenteriae | S. boydii | EIEC |
|---|---|---|---|---|---|---|
| Control 56 | Not Done | Not Done | .165 ± .056 | .035 ± .004 | .035 ± .003 | .132 ± .007 |

C. Serum IgG antibody response to Water Extract Antigen (Vir+) in guinea pigs immunized with Invaplex 50 from different *Shigella* species or EIEC

| 0 | .040 ± .005 | .032 ± .003 | .100 ± .018 | .054 ± .003 | .130 ± .058 | .072 ± .005 |
| 28 | .198 ± .085 | .147 ± .038 | .996 ± .047 | .146 ± .047 | .281 ± .055 | .626 ± .141 |
| 42 | .629 ± .105 | 1.047 ± .153 | 2.347 ± .394 | .856 ± .327 | 1.078 ± .114 | 2.091 ± .219 |
| 56 | 1.914 ± .374 | 3.1 ± .091 | 2.956 ± .280 | 1.836 ± .305 | .817 ± .217 | 2.689 ± .284 |
| Control 0 | .036 ± .006 | .052 ± .017 | .091 ± .019 | .056 ± .006 | .078 ± .004 | .077 ± .009 |
| Control 56 | .377 ± .131 | .93 ± .204 | .072 ± .017 | .135 ± .075 | .048 ± .017 | .059 ± .016 |

D. Serum IgG antibody response to Water Extract Antigen (Vir−) in Gguinea pigs immunized with Invaplex 50 from different *Shigella* species or EIEC

| 0 | .041 ± .005 | .03 ± .003 | .083 ± .013 | .040 ± .002 | .102 ± .039 | .071 ± .006 |
| 28 | .113 ± .040 | .145 ± .044 | 1.014 ± .431 | .131 ± .040 | .225 ± .029 | .511 ± .147 |
| 42 | .497 ± .237 | 1.077 ± .189 | 1.888 ± .505 | .614 ± .225 | .829 ± .137 | 1.767 ± .191 |
| 56 | 1.000 ± .388 | 3.199 ± .097 | 2.465 ± .436 | 1.157 ± .258 | .576 ± .169 | 2.374 ± .319 |
| Control 0 | .037 ± .003 | .036 ± .006 | .062 ± .009 | .043 ± .004 | .059 ± .002 | .086 ± .013 |
| Control 56 | .247 ± .080 | .406 ± .051 | .078 ± .021 | .169 ± .117 | .041 ± .012 | .060 ± .016 |

E. Serum IgG antibody response to Invaplex 24 in guinea pigs immunized with Invaplex 50 from different *Shigella* species or EIEC

| 0 | .046 ± .005 | Not Done | .050 ± .006 | .131 ± .041 | .039 ± .003 | .029 ± .005 |
| 28 | .101 ± .045 | Not Done | .065 ± .009 | .132 ± .035 | .080 ± .031 | .070 ± .018 |
| 42 | .143 ± .030 | Not Done | .149 ± .020 | .140 ± .031 | .604 ± .253 | .225 ± .067 |
| 56 | 1.962 ± .224 | Not Done | .459 ± .030 | .695 ± .173 | 1.287 ± .176 | .739 ± .288 |
| Control 0 | .067 ± .014 | Not Done | .037 ± .003 | .039 ± .003 | .055 ± .010 | .036 ± .002 |
| Control 56 | .216 ± .071 | Not Done | .046 ± .004 | .066 ± .017 | .084 ± .020 | .061 ± .005 |

F. Serum IgG antibody response to Invaplex 50 in guinea pigs immunized with Invaplex 50 from different *Shigella* species or EIEC

| 0 | .050 ± .006 | Not Done | .067 ± .022 | .069 ± .008 | .049 ± .005 | .029 ± .003 |
| 28 | .149 ± .043 | Not Done | .333 ± .064 | .123 ± .024 | .106 ± .019 | .164 ± .031 |
| 42 | .389 ± .155 | Not Done | .742 ± .081 | .373 ± .116 | .925 ± .231 | .530 ± .060 |
| 56 | 2.201 ± .375 | Not Done | 1.573 ± .189 | .904 ± .221 | 2.187 ± .335 | 1.425 ± .313 |
| Control 0 | .049 ± .003 | Not Done | .042 ± .003 | .053 ± .004 | .040 ± .004 | .034 ± .004 |
| Control 56 | .751 ± .107 | Not Done | .100 ± .010 | .155 ± .020 | .066 ± .012 | .073 ± .018 |

TABLE 4. Serum Immune Response to Select Antigens in Guinea Pigs Immunized with Invaplex 50
Different groups of 5 guinea pigs were immunized intranasally on days 0, 14, and 28 with Invaplex 50 prepared from either *S. flexneri* 2a, *S. flexneri* 5, *S. sonnei*, *S dysenteriae*, *S. boydii* 2, or enteroinvasive *E. coli* (EIEC). The Invaplex source is listed at the top of each column. Antigens used in the ELISAs included LPS (TABLE 4A and 4B) prepared from the homologous *Shigella* serotype from which the Invaplex vaccine was prepared; water extract (TABLE 4C and 4D) was from *S. flexneri* 5 vir+ and vir−; and Invaplex 24 (TABLE 4E) and Invaplex 50 (TABLE 4F) were prepared from the same serotype from which the immunizing Invaplex was prepared. The serum IgG levels were measured for each of these antigens by ELISA. The serum IgA levels were solely determined for LPS. Blood was taken from all guinea pigs at 4 different time points, pre-treatment (day 0), post-2nd immunization (day 28), after 3 immunizations (day 42) and 1 week post-challenge (day 56). Animals were challenged with the same *Shigella* serotype from which the Invaplex vaccine was derived. The values for each time-point represents the mean $O.D._{405}$ ± S.E.M. for each group of 5 guinea pigs.

EXAMPLE 4
Adjuvanticity of Invaplex 24 and Invaplex 50

Experiments were performed in mice to evaluate the Invaplex preparations as mucosal adjuvants. Cholera toxin, a proven mucosal adjuvant was used as a positive adjuvant control. The experimental antigen, ovalbumin, was used in these experiments. Ovalbumin is unable to stimulate a substantial antibody response when delivered by itself at a mucosal site.

Figure 6A:
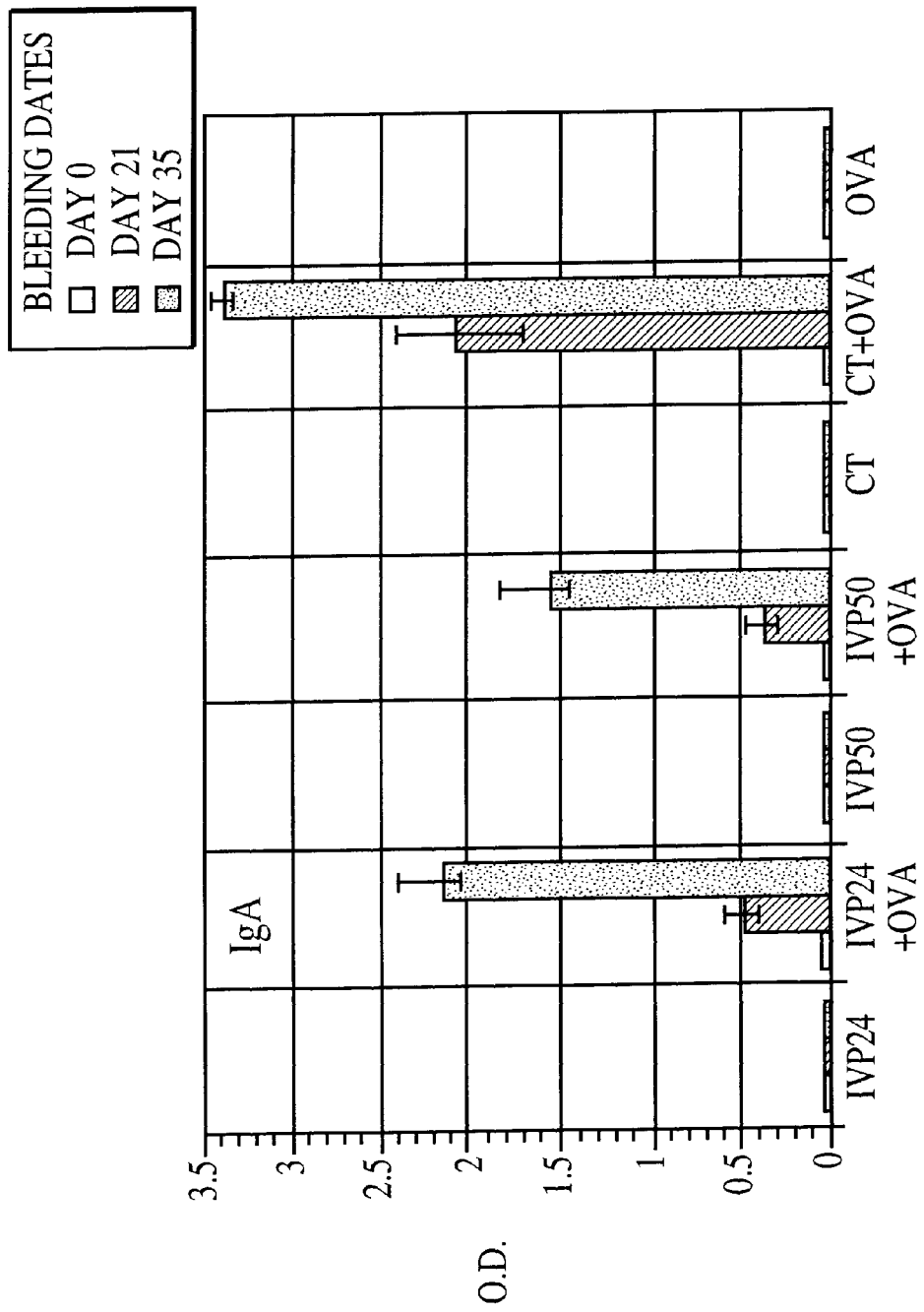
FIGS. 6(A,B). Serum IgA and IgG response to ovalbumin in mice immunized with ovalbumin alone or ovalbumin mixed with Invaplex 24, Invaplex 50, or CT adjuvants. Groups of 5 mice were immunized intranasally three times on days 0, 14 and 28 with adjuvant alone [Invaplex 24 (IVP24); Invaplex 50 (IVP50); or cholera toxin (CT)], adjuvant plus ovalbumin [Invaplex 24 plus ovalbumin (IVP24+ova); Invaplex 50 plus ovalbumin (IVP50+ova); or cholera toxin plus ovalbumin (CT+ova)], or ovalbumin alone (ova). The serum IgA (FIG. 6A) or IgG (FIG. 6B) reactive with ovalbumin was determined by ELISA. The O.D. values are on the vertical axis. The bars for each timepoint (day 0, 21, and 35) represent the mean $O.D._{405}\pm S.E.M.$ for each group of 5 mice.
Figure 6B:
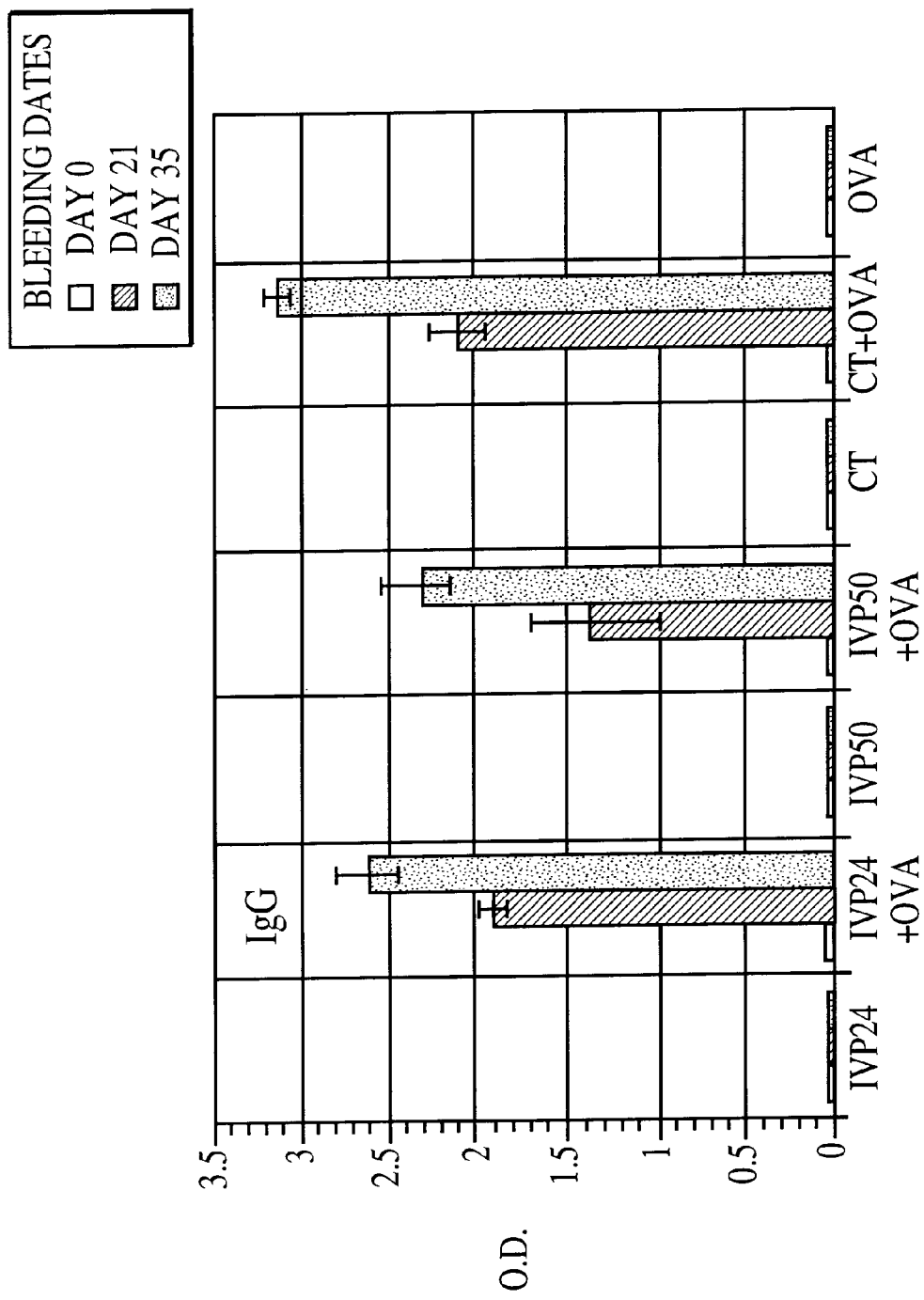

Mice immunized intranasally with ovalbumin alone do not produce a detectable serum IgA (FIG. 6A) or IgG (FIG. 6B) response after 2 or 3 doses of antigen. Mice immunized with an Invaplex 24 plus ovalbumin or Invaplex 50 plus ovalbumin mixture produced pronounced serum IgA (FIG. 6A) and IgG (FIG. 6B) responses against ovalbumin. This antibody response was comparable to a cholera toxin (a proven adjuvant) plus ovalbumin mixture. Invaplex 24 or Invaplex 50 or CT alone did not stimulate an anti-ovalbumin response in these mice.

Figure 7:
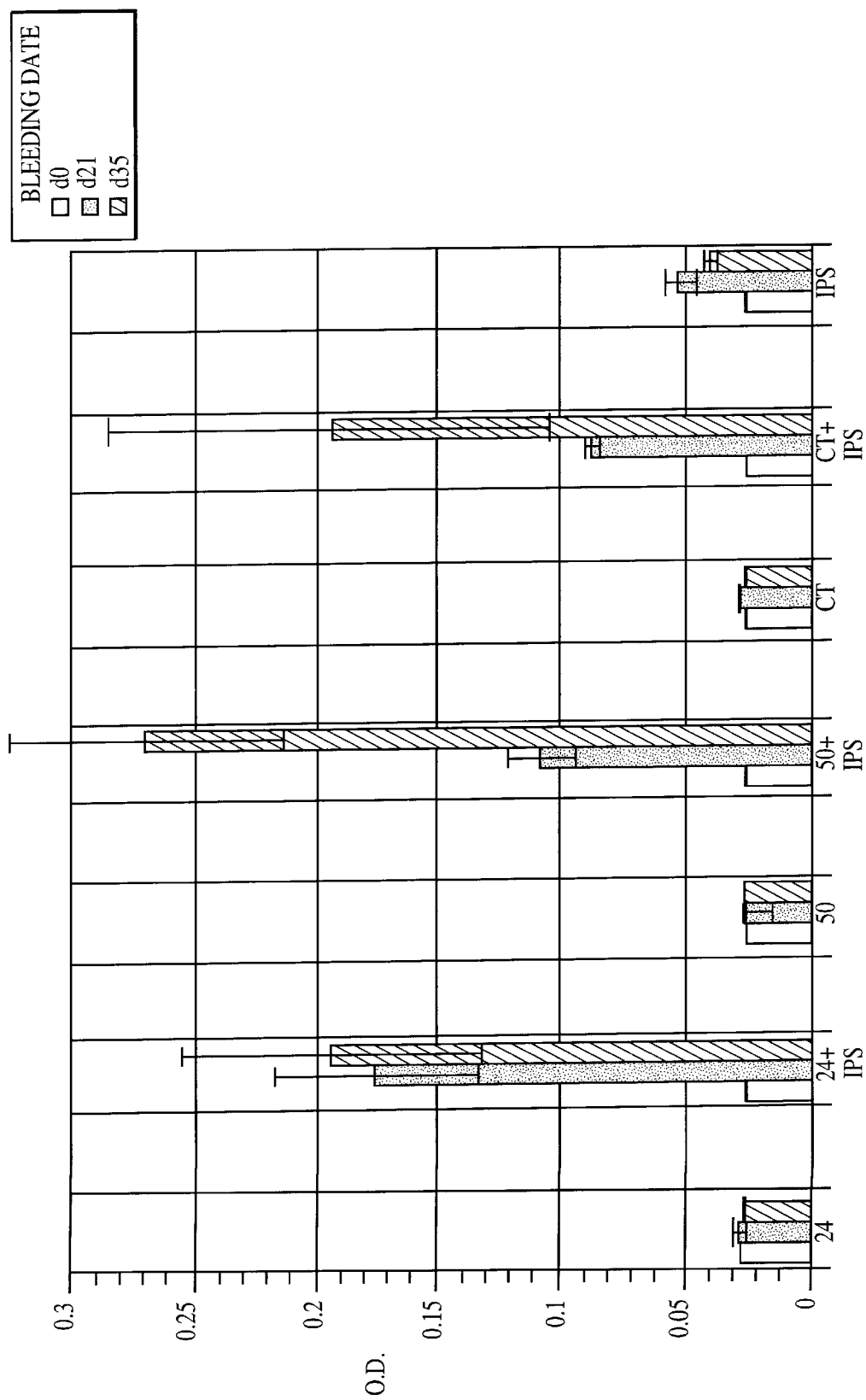
FIG. 7. Serum IgA response to *Shigella sonnei* LPS in mice immunized with LPS alone or LPS mixed with Invaplex 24, Invaplex 50, or CT adjuvants. Groups of 5 mice were immunized intranasally three times with adjuvant alone Invaplex 24 (24); Invaplex 50 (50); cholera toxin (CT); adjuvant plus *S. sonnei* LPS (Invaplex 24 plus LPS (24+1 ps); Invaplex 50 plus LPS (50+1 ps); cholera toxin plus LPS (CT+1 ps), or LPS alone (1 ps). The serum IgA reactive with *S. sonnei* LPS was determined by an ELISA. The O.D. values are in the vertical axis. Blood was taken from all mice at 3 different time points; pre-immunization (day 0), post-second immunization (day 21), and after 3 immunizations (day 35). The bars for each timepoint represent the mean $O.D._{405}\pm S.E.M.$ for each group of 5 mice. Invaplex 24 and Invaplex 50 preparations used in these experiments were isolated from *S. flexneri* 5.
Figure 8:
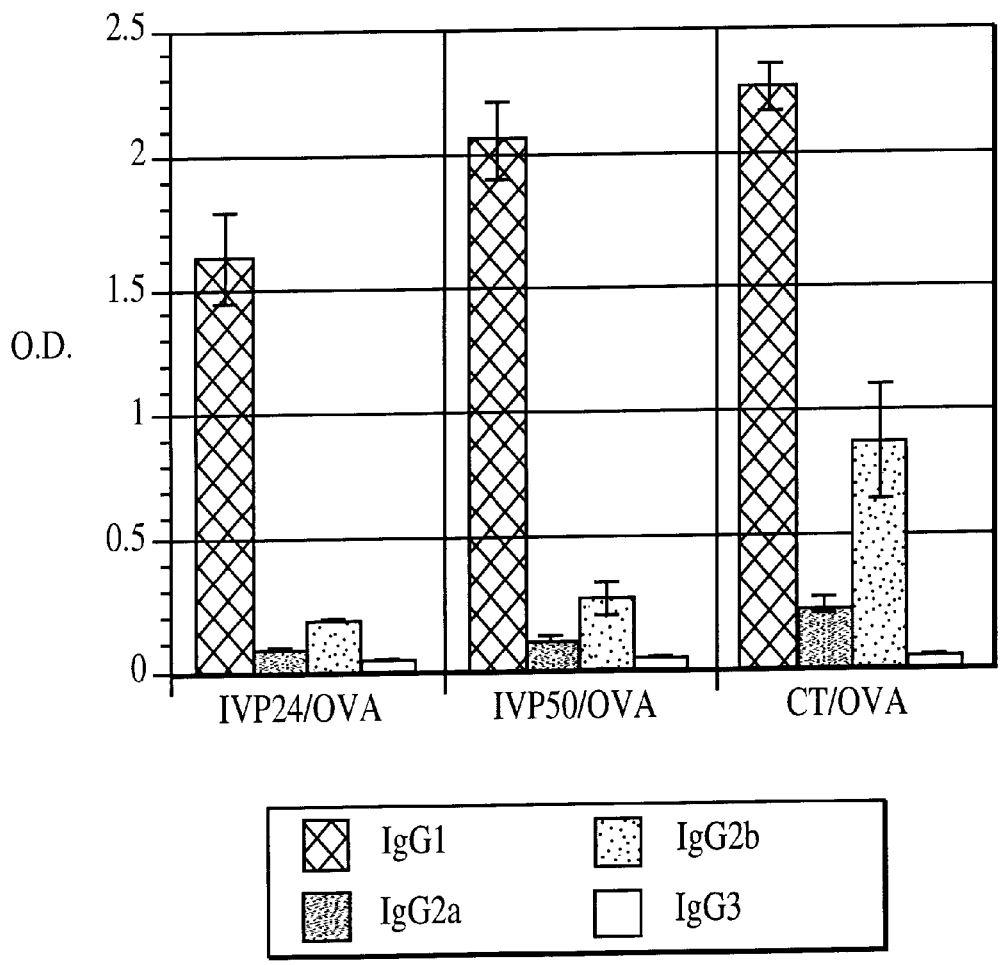
FIG. 8. Serum IgG subclass analysis in mice immunized with ovalbumin mixed with either Invaplex 24, Invaplex 50, or CT adjuvants. Serum from groups of 5 mice, immunized intranasally three times (d0, d14, and d28) with ovalbumin mixed with either Invaplex 24 (IVP24/OVA), Invaplex 50 (IVP24/OVA), or cholera toxin (CT/OVA) was measured for IgG subclasses (IgG1, IgG2a, IgG2b, and IgG3) reactive with ovalbumin in serum collected on d42. The bars for each IgG subclass represent the mean $O.D._{405}\pm S.E.M.$ for each group of 5 mice. Serum was diluted 1/720 for this analysis.

In addition to the protein antigen ovalbumin, it was determined if the Invaplex preparations could enhance the immune response to LPS. Co-administration of purified *S. sonnei* LPS (10 ug) with Invaplex 24 or Invaplex 50 produced a strong serum IgA response to LPS (see FIG. 7). This result was comparable to that produced by CT plus LPS. LPS by itself did not produce a significant IgA response.

The potent adjuvanticity of Invaplex 24 and Invaplex 50 suggested that it may be stimulating the immune response in a manner similar to CT. CT has been shown to stimulate a Th2 T cell response in mice. This has been shown for many different antigens adjuvantized by CT. One characteristic of a Th2 response is increased levels of IL4. This interleukin also has an effect on the subclass of IgG produced against the target antigen. For example relatively high levels of IgG1 are produced against ovalbumin in mice immunized with CT plus ovalbumin. To determine if the Invaplex adjuvants stimulate an IgG subclass similar to CT, the IgG subclasses were measured in mice immunized with Invaplex plus ovalbumin and compared to mice immunized with CT plus ovalbumin mixtures. The anti-ovalbumin response in mice immunized with Invaplex 24 plus ovalbumin or Invaplex 50 plus ovalbumin was characterized by high levels of IgG1 subclass and very low levels of IgG2a, IgG2b, and IgG3. This IgG subclass pattern was almost identical to that generated in mice immunized with CT plus ovalbumin.

Thus Invaplex 24 and Invaplex 50 have strong adjuvant properties capable of stimulating both IgG and IgA response. The adjuvant effect of Invaplex 24 and Invaplex 50 is comparable to CT, a proven mucosal adjuvant. The predominant IgG1 subclass response elicited by Invaplex 24 and Invaplex 50 is very similar to that elicited by CT. This IgG subclass pattern is indicative of increase levels of IL4, a Th2 cytokine.

Furthermore, unlike CT which caused lethargy and ruffled fur in immunized mice, neither Invaplex 24 and Invaplex 50 exhibited any toxicity in mice.

EXAMPLE 5

Dose Response Experiments with The Invaplex 24 and Invaplex 50 Vaccines

Figure 9A:
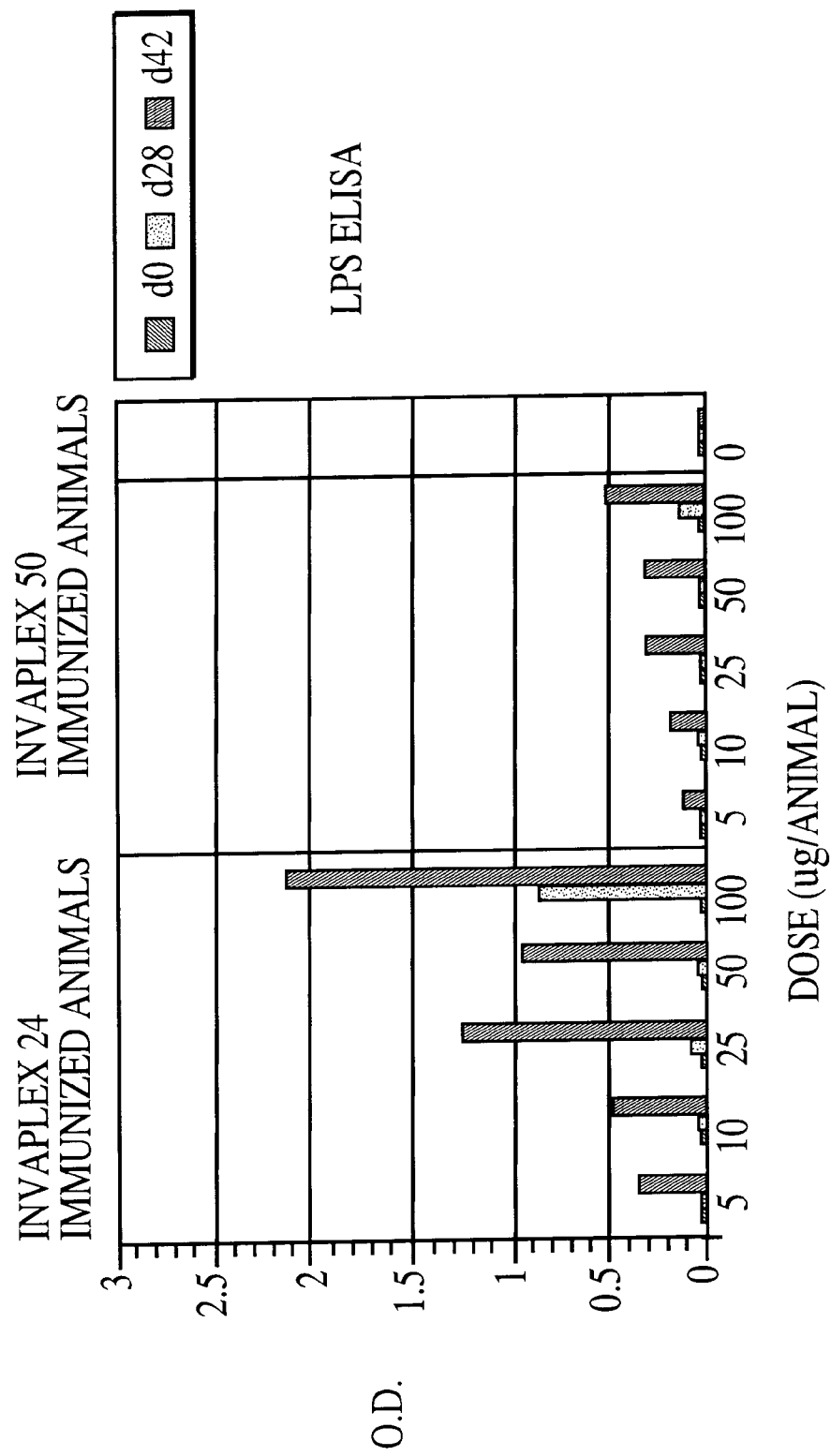
FIGS. 9(A–E). Antibody response to LPS and water extract in guinea pigs immunized with different doses of Invaplex 24 or Invaplex 50 vaccine. 5 groups of guinea pigs (4 animals per group) were immunized with either 0, 5, 10, 25, 50 or 100 ug/dose of *S. flexneri* 2a Invaplex 24 or Invaplex 50. Guinea pigs were immunized intranasally on days 0, 14, and 28; blood was collected on days 0, 28, and 42. The serum IgG response was measured by ELISA against *S. flexneri* 2a LPS (FIG. 9A), water extract from Vir+ (9B) and Vir− (FIG. 9C) shigellae. In each of the 3 panels, the Invaplex 24 immunized animal data are on the left, the Invaplex 50 immunized animal data are in the middle, and the buffer control animal data are on the right side of each graph. The bars represent the mean $O.D._{405}\pm S.E.M.$ for each group of 4 guinea pigs. The vaccine dosage (ug) is indicated below the data for each group of guinea pigs.
FIGS. 9D and 9E. Antibody response to Invaplex 24 and Invaplex 50 in guinea pigs immunized with different doses of Invaplex 24 or Invaplex 50 vaccine. 5 groups of guinea pigs (4 animals per group) were immunized with either 0, 5, 10, 25, 50 or 100 ug/dose of S. flexneri 2a Invaplex 24 (FIG. 9D) or Invaplex 50 (FIG. 9E). Guinea pigs were intranasally immunized on days 0, 14, and 28; blood was collected on days 0, 28, and 42. The serum IgG response for all groups was measured by ELISA against both S. flexneri 2a Invaplex 24 (left hand side of top and bottom panel) and S. flexneri 2a Invaplex 50 (right-hand side of the top and bottom panel). The bars represent the mean $O.D._{405} \pm S.E.M.$ for each group of 4 guinea pigs. The vaccine dosage (ug) is indicated below the data for each group of guinea pigs.

Experiments were conducted to determine the immunogenicity of the S. flexneri 2a Invaplex 24 and Invaplex 50 vaccines. Guinea pigs (4 per group) were immunized with either 0, 5, 10, 25, 50, or 100 ug of Invaplex per dose. Each animal was immunized intranasally 3 times at two week intervals. Several different ELISAs were used to measure the antibody response generated in response to the different doses of Invaplex (FIGS. 9(A–E)). Against LPS gradually higher levels of anti-LPS IgG were present with increasing doses of Invaplex (FIG. 9A). The Invaplex 24 vaccine produced somewhat higher anti-LPS levels than the Invaplex 50 vaccine. At the 100 ug dose, a positive anti-LPS response is present after two doses of vaccine. At lower doses a positive anti-LPS response is not detectable until after three immunizations.

Figure 9B:
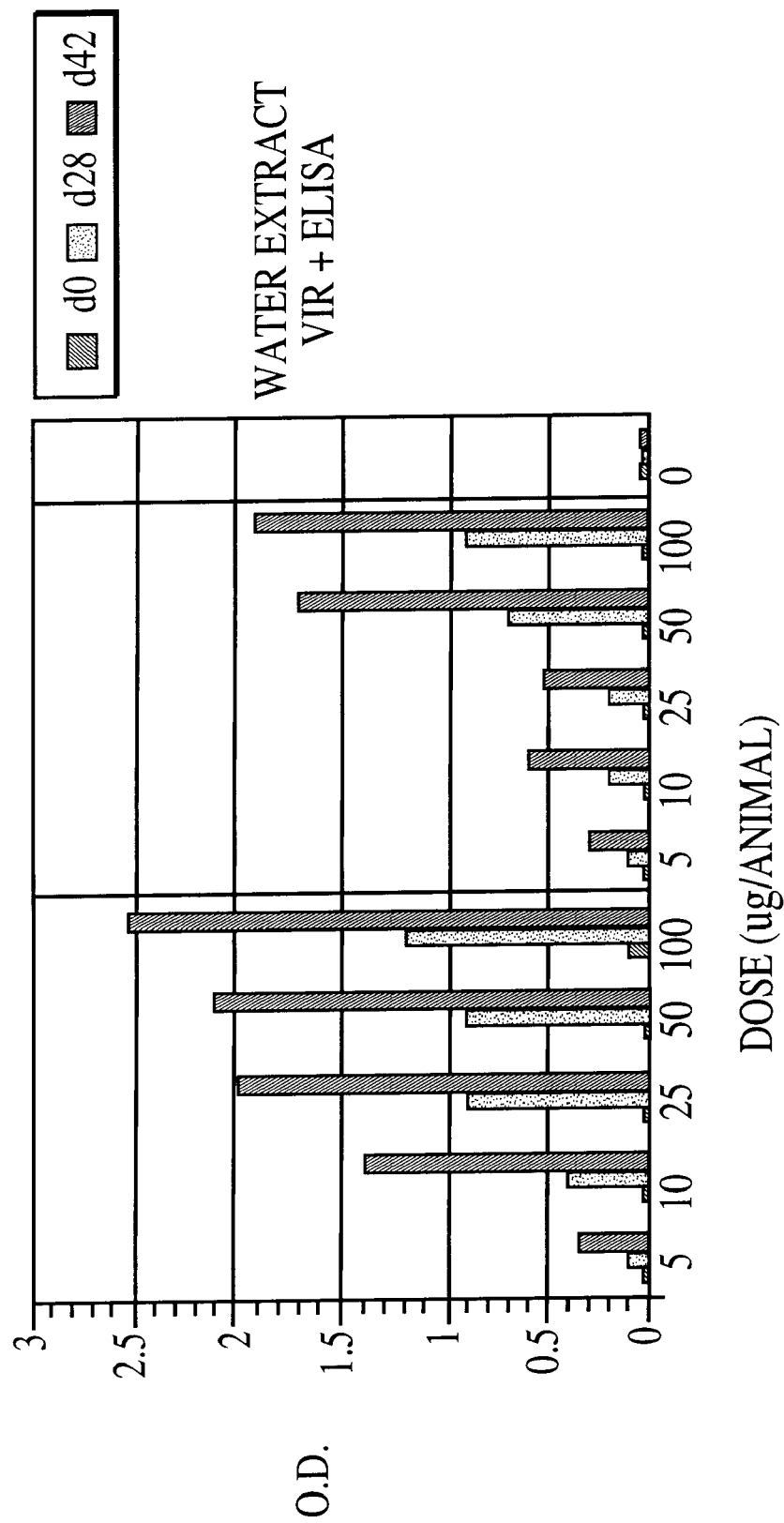
Figure 9C:
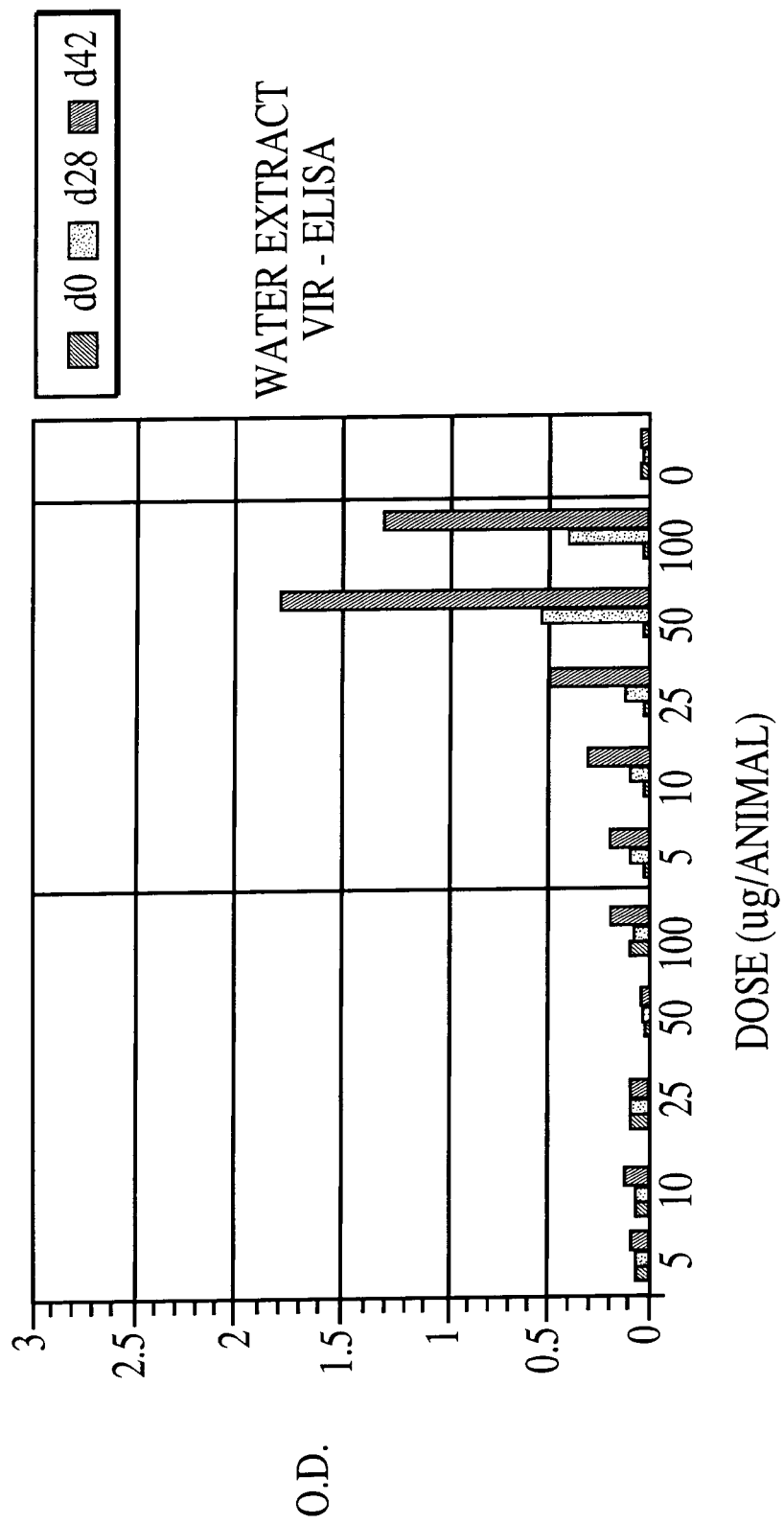

Higher levels of antibodies reactive with the water extract were evident in the animals receiving higher doses of Invaplex (FIGS. 9B and 9C). However antibodies to the water extract antigen were detected in the lowest dose of (5 ug) group after 3 immunizations. Positive antibody responses against the vir+ water extract were evident in all dose groups for Invaplex 24 after just 2 doses, while for Invaplex 50 a positive antibody response after 2 doses was evident in animals immunized with 25 ug of Invaplex of above. As noted above, Invaplex 24, at all doses, produced a striking virulence specific antibody response, whereas Invaplex 50 produced antibodies reactive with both vir+ and vir− water extract antigens. The Invaplex 50 response occurred at all doses.

Figure 9D:
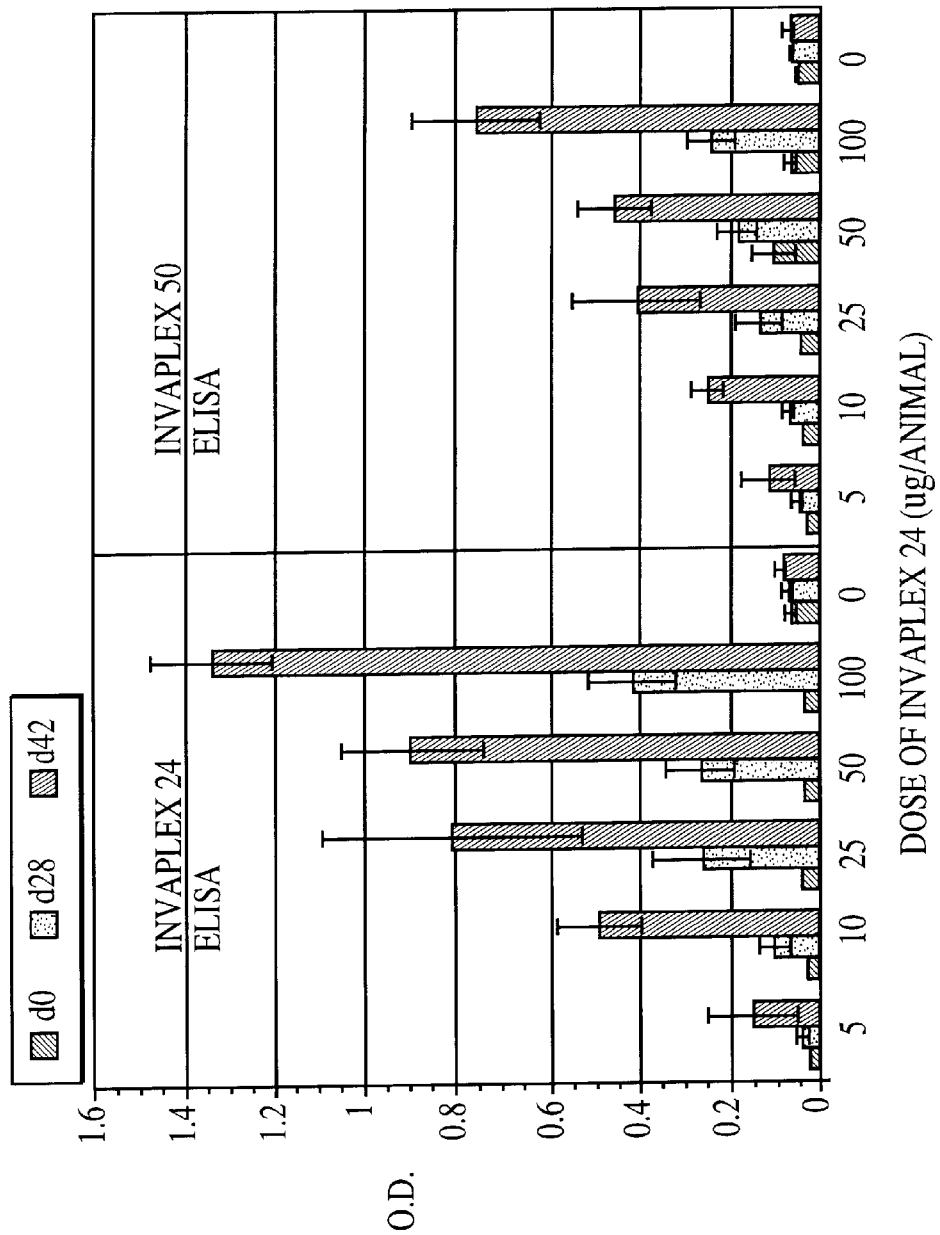
Figure 9E:
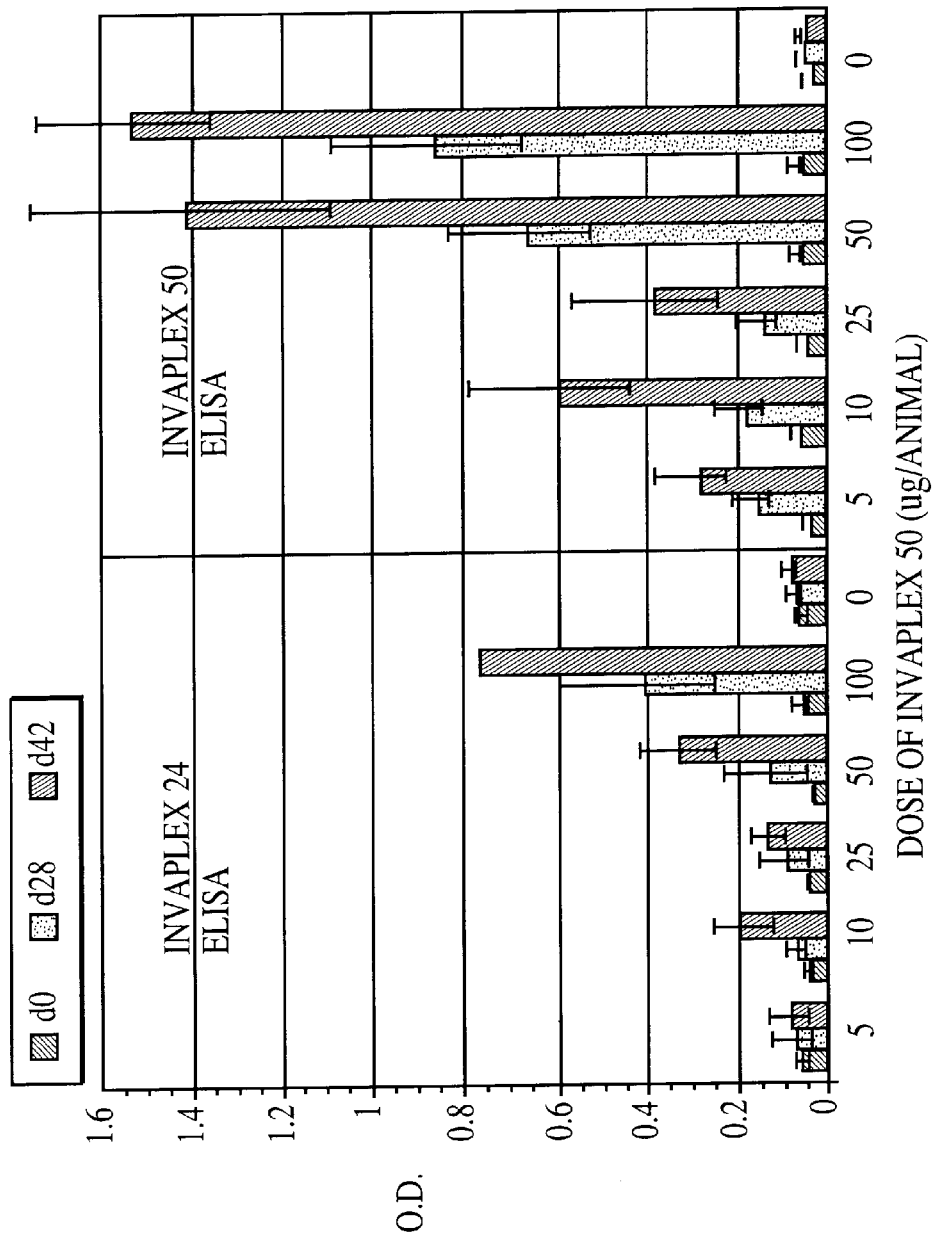

Antibodies reactive with the homologous Invaplex used for immunization were also measured in the dosing experiment guinea pigs (FIGS. 9D and 9E). As shown above for LPS and water extract ELISAs, the level of antibodies reactive with the Invaplex antigens increased with the higher doses of Invaplex vaccine. Antibodies reactive with Invaplex 24 (FIG. 9D) were present in all animals immunized with 3 doses of Invaplex 24, and were only detected after two doses in animals immunized with 25 ug or higher. Lower levels of antibodies in the Invaplex 24 immunized animals sera were detected in the Invaplex 50 ELISA but in general followed a dose response curve with higher levels of antibodies corresponding to higher vaccine doses. Similar results were evident in the Invaplex 50 ELISA (FIG. 9E) in that higher doses of Invaplex 50 vaccine stimulated higher levels of antibodies in immunized animals. The lowest dose tested (5 ug) was capable of stimulating a measurable antibody response.

EXAMPLE 6

Safety and Side-Effects of the Invaplex 24 and Invaplex 50

Animals (guinea pigs or mice) intranasally immunized with Invaplex 24 or Invaplex 50 showed no visible side effects (fur ruffling, lethargy, diarrhea) after immunization. In mice this lack of toxicity was observed at doses of 5 and 10 ug and for guinea pigs the lack of toxicity was evident for doses ranging from 5 ug up to 100 ug. In addition guinea pigs immunized with either Invaplex 24 or Invaplex 50 gained weight at a comparable rate to guinea pigs treated with normal saline. This indicates that water intake and food intake was normal for these animals. Weight gain was not measured in mice but there was no apparent lack of weight gain in mice immunized with the Invaplex 24 or Invaplex 50 preparations.

EXAMPLE 7

Invaplex as a Diagnostic Tool, Use as an Antigen in ELISAs

The water extract antigen has often been used to measure the antibody response to the virulence associated antigens (Ipa proteins) in an ELISA format (Oaks, et al., 1986, Infect. Immun. 53, 57–63; Li et al., 1993, Scand. J. Infect. Dis. 25, 569–577).

In preliminary experiments to determine the presence and reactivity of various Shigella antigens, monoclonal antibodies or polyclonal sera were used in the Invaplex ELISA. These experiments indicated that epitopes of IpaB, IpaC, IpaD, and LPS are all available and reactive in both Invaplex 24 and Invaplex 50 ELISA assays. In addition, pooled monkey sera (pre and post-challenge) were also evaluated, and found to have significantly higher antibody levels present in the convalescent sera as compared to the pre-challenge sera.

In a more extensive experiment, pre- and post-challenge sera collected from monkeys infected with S. flexneri 2a were evaluated in the Invaplex 24 and Invaplex 50 ELISAs (see Table 5). In studies M218 and M219 monkeys were infected with different doses of virulent S. flexneri 2a. For assessing the effectiveness of the Invaplex as an ELISA antigen it was used to measure the antibody response in animals that received subclinical doses of shigellae to determine if antibodies could be detected in the absence of disease. The results are compared to similar studies done with other ELISA antigens such as LPS, water extract, and recombinant IpaC (Table 5). Monkeys infected with sub-clinical doses of virulent shigellae (both groups in M218 and the lower dose in study M219) produced IgG antibodies reactive with the Invaplex antigens used in an ELISA. Seroconversion was detected with Invaplex 24 and Invaplex 50 at about the same rate as that detected by water extract, but the Invaplex ELISA detected more positives than did the LPS ELISA. At the highest dose of virulent shigellae in which most (10/11) of the animals got sick, almost every animal was positive as determined by ELISAs for LPS, water extract, Invaplex 24 or Invaplex 50.

Monkeys vaccinated with the live, attenuated S. flexneri 2a vaccine called SC602 (Barzu et al., 1998, Infect. Immun. 66, 77–82) seroconverted as detected by ELISAs for LPS (16/16), water extract (15/16), and Invaplex 50 (15/16) (Table 5). Only 3 of 16 animals were positive in the Invaplex 24 ELISA. In the control group which consisted of animals challenged with virulent S. flexneri 2a, almost all animals seroconverted as determined by LPS (7/7), water extract (6/7) and Invaplex 50 (7/7) ELISAs. Five of seven animals were positive in the Invaplex 24 ELISA.

It appears that the Invaplex ELISAs, in particular the Invaplex 50 antigen, are useful in detecting a serum antibody response in animals with subclinical Shigella infections. In cases of apparent disease the Invaplex ELISAs are comparable to LPS or water extract ELISAs.

EXAMPLE 8

Further Purification of Invaplex 24 and Invaplex 50 by Gel Filtration Chromatography Gel filtration chromatography was used to further purify the Invaplex collected from ion-exchange chromatography fractions. Invaplex samples were applied to a Superose 6 HR10/30 column (Pharmacia, Uppsala, Sweden) equilibrated with 20 mM Tris-HCl (pH 9) containing 0.24M NaCl (for Invaplex 24 separations) or 0.5 M NaCl (for Invaplex 50 separations). Fractions (0.5 ml) were collected and analyzed for the presence of IpaB, IpaC, and LPS using immuno spot-blots, western blots, or silver stained polyacrylamide gels. The column was standardized with proteins of known molecular weights.

For Invaplex 24, a large complex (greater than 670,000 mw) containing LPS, IpaB and IpaC was found. The fractions containing this large molecular weight complex were separated from smaller sized protein-containing fractions.

For Invaplex 50, a large complex (greater than 670,000 mw) containing LPS, IpaB and IpaC was also found. The fractions containing this large molecular weight complex were separated from smaller sized protein-containing fractions.

Discussion

Shigellosis is a leading cause of human diarrheal disease. Each year millions of cases occur particularly in developing countries and it is estimated that over 1 million cases result in death (Kotloff et al., 1999, *Bull. WHO* 77, 651–666). The constant emergence of antibiotic resistance in Shigella, even to the newest antibiotics, underscores the need for an effective vaccine to help control Shigella disease. Unfortunately, vaccine strategies must consider the need for protection against 4 species of Shigella (*S. flexneri, S. sonnei, S. dysenteriae,* and *S. boydii*) as well as enteroinvasive *E. coli* as cross-protection is not significant. Compounding this problem is the fact that there are over 45 different serotypes and the level of protective cross-reactions between these serotypes is not known. Present vaccine strategies include living attenuated vaccines (Coster, et al., 1999, *Infect. Immun.* 67, 3437–3443) and also delivery of Shigella LPS or O-polysaccharides with carriers such as proteosomes (Orr et al., 1993, *Infect. Immun.* 61, 2390–2395) or protein carriers such as tetanus toxoid (Polotsky, et al., 1994, *Infect. Immun.* 62, 210–214).

The protective immune response which is necessary to prevent future Shigella infections is not completely understood. In natural infections the immune system produces antibodies to LPS and to several virulence proteins, including IpaC, IpaB, and at lower frequency IpaD, IpaA and VirG. Recent studies have indicated that the Shigella virulence proteins or invasins actually are associated together in a complex, and it is hypothesized that this complex is the functional entity involved in the invasive event (Menard et al., 1996, *Proc. Natl. Acad. Sci. USA* 93, 1254–1258). It is not known if the invasin complex is recognized as an intact structure by the immune system but if it is then it is very likely that invasin-complex antibodies may occur. Such antibodies could have a role in neutralizing invasive shigellae.

The recently reported IpaB:IpaC structure (Menard et al., 1996, *Proc. Natl. Acad. Sci. USA* 93, 1254–1258) was found in culture medium. It is not clear if this IpaB:IpaC complex found in culture medium is actually the active structure involved in the invasive event. It is more likely that the active complex resides on the surface of the shigellae and will be activated and released upon exposure to the proper stimulus such as close proximity of a host cell or detection of a host cell biochemical indicating a host cell is nearby. In this study a novel method has been developed for isolating a macromolecular structure containing the major known virulence factors and immunogens from intact, viable, virulent shigellae. This structure is called the invasin complex or "Invaplex" and it contains the invasins (Ipa proteins) and LPS. Two forms of the Invaplex have been isolated by FPLC ion-exchange chromatography. They are the Invaplex 24 and Invaplex 50 preparations. Both Invaplex 24 and Invaplex 50 contain IpaB, IpaC, IpaD, IpaA and LPS. VirG*, a truncated form of VirG, is found only in Invaplex 50. Invaplex 24 and Invaplex 50 have been isolated from all 4 species of Shigella and also EIEC. Invaplex 24 or Invaplex 50 derived from each species is similar with respect to Ipa protein content and LPS content. Run to run consistency is very high making the production of Invaplex a reproducible procedure.

The availability of a subunit preparation derived from shigellae which contains the major antigens and virulence factors provides a reagent that could be used for the measurement of the immune response to an intact virulence structure and also provides a novel subunit approach to Shigella vaccines.

Our studies indicate that both Invaplex 24 and Invaplex 50 are very immunogenic in mice and in guinea pigs. Intranasal immunizations, without any additional adjuvant, stimulated both an IgA and IgG response to LPS, and to antigens in the water extract ELISA antigen. This includes IpaC, IpaB and other virulence proteins. Interestingly, Invaplex 24 produced a virulent specific antibody response very similar to that produced in monkeys or humans infected with Shigella spp. (Oaks et al., 1986, *Infect. Immun.* 53, 57–63) Invaplex 50 stimulated a serum antibody response which was not virulent specific (as measured by the water extract ELISA). This indicates that non-plasmid encoded antigens are in the Invaplex 50 and are capable of stimulating an antibody response. Even so, Invaplex 50 preparations do stimulate antibodies to virulence proteins such as IpaC and IpaB, as determined by western blot analysis of immune sera. Invaplex preparations from all species of Shigella were capable of stimulating an antibody response to the homologous immunizing Invaplex as measured by ELISA. Animals immunized with Invaplex 24 always had higher antibody levels to the immunizing antigen (i.e., Invaplex 24) than to the analogous (i.e., same shigella serotype) Invaplex 50 antigen. In the reciprocal situation, Invaplex 50 animals had higher antibody levels against the immunizing Invaplex 50 antigen than to the analogous (i.e., same Shigella serotype) Invaplex 24 antigen. These results are good evidence that the Invaplex 24 and Invaplex 50 contain unique antigens or possibly present antigens in a unique way resulting in a dominant immune response against the immunizing Invaplex. The unique immune response elicited to the two Invaplex preparations may be in part to the presence of VirG* in only the Invaplex 50 preparations.

Potent immune responses were achieved with small quantities of Invaplex. In mice, 5 or 10 ug, and in guinea pig 25 ug were capable of producing measurable antibody levels after 3 intranasal immunizations. In dose response experiments using *S. flexneri* 2a Invaplex 24 and Invaplex 50, it was possible to stimulate a measurable antibody response to LPS, water extract, or Invaplex with three, 5 ug dose of vaccine. Higher doses (25, 50 and 100 ug) generated a positive antibody response after 2 intranasal doses. In all cases, animals immunized with Invaplex 24 or Invaplex 50, showed a dramatic increase in antibody levels upon challenge with virulent shigellae of the identical serotype of Invaplex vaccine. This rapid boost in titer (post-challenge blood was collected one week after challenge) is a result of the effective priming of the immune system by the Invaplex vaccines.

Delivering vaccines by the mucosal route (intranasal, oral, etc) is difficult and not very effective unless suitable mucosal adjuvants are used. The potent immune response generated by the Invaplex preparations and the known capacity of the Ipa proteins to interact with host cells suggest that the Invaplex might be able to enhance the immune response to co-administered antigens, somewhat like cholera toxin. The best mucosal adjuvant is cholera toxin in that it enhances a pronounced IgA response in secretions and blood as well as a serum IgG response. It has been established in mice, that the underlying immune mechanism stimulated by cholera toxin adjuvanticity is based on a T helper 2 (Th2) response. This is characterized by increased levels of cytokines IL4 and IL5 which are released by activated T cells. This leads to increased levels of secretory and serum IgA. One effect of IL4 is that it promotes an IgG1 response (in mice) to the immunizing antigen. For example in mice immunized with a CT/ovalbumin mixture, the predominant immunoglobulin G subclass is IgG1 with low levels of IgG2b also being made against ovalbumin (Marinaro et al, 1995, supra). IgG2a and IgG3 are not stimulated by CT/ovalbumin after intranasal immunization. To determine the adjuvanticity of Invaplex 24 and Invaplex 50 mixtures of ovalbumin and Invaplex were administered intranasally to mice. Our results indicate that both Invaplex 24 and Invaplex 50 behave as adjuvants in that they enhanced the immune response to an otherwise non-immunogenic substance (i.e., ovalbumin). The antibody response to ovalbumin generated by ovalbumin/Invaplex mixtures was comparable to ovalbumin mixed with CT, a known mucosal adjuvant. Furthermore IgG subclass analysis of the anti-ovalbumin IgG response showed that the predominant IgG subclass generated was IgG1 which is indicative of a Th2 response. The IgG subclass response elicited by Invaplex/ovalbumin mixtures was almost identical to that produced in response to CT/ovalbumin mixtures. Additional characteristics of Th2 responses is increased IgA levels (Marinaro et al., 1995) as a result of increased levels of IL-5. IgA levels were prominant in Invaplex immunized animals and furthermore Invaplex immunized animals are protected from challenge in the kerato-conjunctivitis assay which is a mucosal challenge.

What is claimed is:

1. An immunogenic composition comprising an isolated lipopolysaccharide-protein complex (Invaplex) isolated from a water extract of gram-negative bacteria, wherein the complex is composed of at least one invasin protein associated with LPS of said gram-negative bacteria.

2. A composition according to claim 1 wherein said gram-negative bacteria is selected from the group consisting of Shigella, Escherichia, Salmonella, Yersinia, Rickettsia, Brucella, Erhlichiae, Edwardsiella, Campylobacter, Legionella and Neisseria.

3. A composition according to claim 1 wherein said Invaplex comprises IpaA, IpaB, IpaC, IpaD and LPS.

4. A composition according to claim 2 wherein said Shigella is selected from the group consisting of *S. flexneri, S. sonnei, S boydii* and *S. dysenteraie*.

5. A composition according to claim 2 wherein said Escherichia is *Escherichia coli*.

6. A composition according to claim 3 wherein said Invaplex further comprises VirG or portions thereof.

7. A composition according to claim 4 wherein said Invaplex comprises at least one invasin protein selected from the group consisting of IpaA, IpaB, IpaC, IpaD and LPS.

8. A composition according to claim 5 wherein said *Escherichia coli* is strain EIEC.

9. A composition according to claim 8 wherein said Invaplex comprises at least one invasin protein selected from the group consisting of Ipaa, IpaB, IpaC, IpaD and LPS.

10. A composition according to claim 8 wherein said Invaplex comprises IpaA, IpaB, IpaC, and LPS.

11. A composition according to claim 10 wherein said Invaplex further comprises IpaD.

12. A composition according to claim 11 wherein said Invaplex further comprises VirG or portions thereof.

13. A method for preparing isolated Invaplex from Shigella, said method comprising the steps of:
    (i) extracting Shigella with water to form an aqueous phase having an immunogenic lipopolysaccharide-protein complex component, Invaplex,
    (ii) separating and discarding membrane fragments from said aqueous phase resulting in a solution containing the Invaplex; and
    (iii) isolating the Invaplex from said solution.

14. The method according to claim 13 wherein said isolating in step (iii) is accomplished by using an ion exchange matrix.

15. A method for preparing isolated Invaplex from Escherichia, said method comprising the steps of:
    (i) extracting Escherichia with water to form an aqueous phase having an immunogenic lipopolysaccharide-protein complex component, Invaplex;
    (ii) separating and discarding membrane fragments from said aqueous phase resulting in a solution containing the Invaplex; and
    (iii) isolating the Invaplex from the solution with an ion-exchange matrix.

16. A method for screening agents or drugs which reduce or eliminate Invaplex said method comprising detecting a dissociation of said Invaplex in the presence of said agent or drug.

17. A method for detecting gram-negative bacterial infection in a biological sample comprising
    (i) contacting a sample with a solid surface to which is attached an Invaplex isolated from bacteria suspected of causing the bacterial infection; and
    (ii) detecting the presence or absence of a complex formed between said isolated Invaplex and antibodies specific therefor in said sample wherein the presence of said complex indicates the presence of said bacterial infection, wherein the isolated Invaplex is an immunogenic lipopolysaccharide-protein complex that has been isolated from a water extract of the gram-negative bacteria, is an adjuvant and is composed of at least one invasin protein associated with LPS of the gram-negative bacteria.

18. The method of claim 17 wherein said biological sample is from an animal.

19. A method to elicit an antigen-specific immune response in a subject, said method comprising administering to said subject an Invaplex isolated from a gram-negative bacteria along with said antigen wherein said antigen-specific immune response is chosen from the group consisting of cell-mediated immune response, humoral immune response, and mucosal immune response, wherein the isolated Invaplex is an immunogenic lipopolysaccharide-protein complex that is isolated from a water extract of gram-negative bacteria, is an adjuvant and is composed of at least one invasin protein associated with LPS of said gram-negative bacteria.

20. The method of claim 19 wherein said antigen is selected from the group consisting of viral antigens, mammalian cell surface molecules, bacterial antigens, fungal antigens, protozoan antigens, parasitic antigens, and cancer antigens.

21. The method of claim 19 wherein said Invaplex is administered by a route selected from the group consisting of intramuscular, bronchial, genital, nasal, oral, parenteral, transcutaneous, transdermal and rectal.

* * * * *